United States Patent
Tsukamoto et al.

(10) Patent No.: US 7,713,722 B2
(45) Date of Patent: May 11, 2010

(54) METHOD FOR IMPROVING ENZYMATIC ACTIVITY OF GLYCOSYLTRANSFERASES

(75) Inventors: Hiroshi Tsukamoto, Iwata (JP); Takeshi Yamamoto, Iwata (JP); Yoshimitsu Takakura, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 3 days.

(21) Appl. No.: 11/665,568

(22) PCT Filed: Sep. 30, 2005

(86) PCT No.: PCT/JP2005/018169

§ 371 (c)(1),
(2), (4) Date: Jan. 28, 2008

(87) PCT Pub. No.: WO2006/043406

PCT Pub. Date: Apr. 27, 2006

(65) Prior Publication Data

US 2009/0087894 A1    Apr. 2, 2009

(30) Foreign Application Priority Data

Oct. 18, 2004    (JP)    ................. PCT/JP2004/015363

(51) Int. Cl.
C12N 9/10    (2006.01)
C12N 9/00    (2006.01)
C12N 1/20    (2006.01)
C12N 15/00    (2006.01)
C07H 21/04    (2006.01)

(52) U.S. Cl. .................... 435/193; 435/183; 435/252.3; 435/320.1; 536/23.2

(58) Field of Classification Search ........................ None
See application file for complete search history.

(56) References Cited

FOREIGN PATENT DOCUMENTS

JP    10-234364 A    9/1998

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Muller et al., "Species-Specific Aggregation Factor in Sponges. Sialyltransferase Associated with Aggregation Factor," J. Biol. Chem., vol. 252, (1977), pp. 3836-3842. (abstract included).
Shimamura A. et al., "Effect of NaCl Concentration on the Activities of Three Glucosyltransferases from Streptococcus Mutans 6715," Bull Natldef. Med. Coll., vol. 9, (1986), pp. 171-178; particularly pp. 173, 9th to 4th line from the bottom; pp. 175, 8th line from the bottom to p. 176, line 5, fig. 1.
Shujunsha, Cell Technology ("Saibou Kougaku"), Supplement, Jul. 1996, pp. 104-107, Tokyo, Japan.
Inouye et al., J.Biochem., (1997), vol. 122, pp. 358-364.

* cited by examiner

Primary Examiner—Christian L Fronda
(74) Attorney, Agent, or Firm—Birch, Stewart, Kolasch & Birch, LLP

(57) ABSTRACT

The present invention provides an inexpensive and simple method which allows efficient glycosylation with glycosyltransferases derived from microorganisms of the Vibrionaceae family when compared to conventional enzymatic reaction systems.

According to the method of the present invention, glycosyltransferases derived from microorganisms of the Vibrionaceae, such as β-galactoside-α2,6-sialyltransferase derived from *Photobacterium damselae*, β-galactoside-α2,3-sialyltransferase derived from *Photobacterium phosphoreum* and β-galactoside-α2,3-sialyltransferase derived from *Vibrio* sp., enhance their enzymatic activity when an appropriate amount of NaCl is added to their enzyme reaction systems.

7 Claims, 3 Drawing Sheets

METHOD FOR IMPROVING ENZYMATIC ACTIVITY OF GLYCOSYLTRANSFERASES

TECHNICAL FIELD

The present invention relates to a method for improving the activity of glycosyltransferases.

BACKGROUND ART

Glycosyltransferases are enzymes involved in in vivo biosynthesis of sugar chains on glycoproteins, glycolipids and the like. Their reaction products, i.e., sugar chains on glycoproteins, glycolipids and the like (hereinafter referred to as "complex carbohydrate sugar chains") have been shown to be important molecules which play a role in cell-cell and cell-extracellular matrix signaling and serve as tags for complex carbohydrates during differentiation and/or development.

An industrial example where sugar chains are applied is a modification of erythropoietin with sugar chains. Although erythropoietin originally has sugar chains, attempts have been made to increase the number of sugar chains on erythropoietin, whereby erythropoietin products with an extended life span in the body have been developed and are commercially available. In the future, such a product modified with sugar chains is expected to be increasingly marketed. For this reason, production of glycosyltransferases will also be important. Moreover, for functional elucidation of complex carbohydrate sugar chains, various sugar chains are required to be synthesized and their mass production will be necessary.

Synthesis techniques for complex carbohydrate sugar chains are generally divided into two major types. The first is a chemical synthetic approach, and the other is an enzymatic approach using a glycosyltransferase. It should be noted that there is also an intermediate approach, i.e., a chemo-enzymatic synthesis technique based on both chemical and enzymatic approaches.

When a comparison is made between chemical synthetic approach and enzymatic approach, they have both merits and demerits.

As to the merits of the chemical synthetic approach, there are many findings about sugar chain synthesis and hence this approach may be flexibly adapted to the synthesis of various sugar chains. However, the chemical synthetic approach is usually required to comprise a protection/deprotection step and, as a consequence, it involves a long synthetic route and complicated operations. Thus, there is a demerit in that a target product cannot be obtained in high yield. Moreover, as stated above, it is believed that sugar chain modification of proteins, lipids and the like will be important in the future, but it is very difficult to achieve sugar addition without impairing functions of proteins and/or lipids in the chemical synthetic approach in light of its synthesis conditions.

On the other hand, the enzymatic approach is advantageous over the chemical synthetic approach in the following points. In the enzymatic approach, reaction steps are very simple and a target product can be obtained in high reaction yield. Further, since the enzymatic approach allows reactions under mild conditions, it can be adapted to sugar chain modification of proteins or lipids without causing their denaturation.

Until now, about 150 or more glycosyltransferase genes have been isolated from eukaryotic organisms including humans, mice, rats and yeast, and proteins having glycosyltransferase activity have also been expressed in production systems where CHO or E. coli cells are used as host cells. However, enzymes produced by these host cells usually show a very low level of specific activity when compared to the specific activity of glycosyltransferases in their native tissues or cells. This is because although glycosyltransferases produced by E. coli or other host cells have the same primary protein structure as native glycosyltransferases produced in animal cells, there is a difference in the structure or the like added to their protein moiety, so that the specific activity of recombinant enzymes will be reduced when compared to native enzymes.

On the other hand, several glycosyltransferase genes have also been isolated from bacteria which are prokaryotic organisms. Moreover, proteins having glycosyltransferase activity have been expressed in production systems using E. coli and identified for their substrate specificity and/or various enzymatic properties. As to an example of stable and mass producible glycosyltransferases derived from such microorganisms, there are reports of β-galactoside-α2,6-sialyltransferase derived from Photobacterium damselae strain JT0160 (Japanese Patent No. 3062409, JP 10-234364 A). The productivity of this enzyme is 550 U per liter of culture solution, and the enzyme can be presented as an example which is mass producible. However, to achieve more efficient sugar chain synthesis, there has been a demand for the development of a novel enzymatic reaction method for increasing enzyme activity.

For measuring the enzyme activity of mammalian-derived sialyltransferases, it is reported that a divalent ion such as $MgCl_2$ or $CaCl_2$ is often added to their reaction systems (Glycobiology Experimental Protocols, Cell Technology, Supplement, July 1996, pp. 104-107, Shujunsha Co., Ltd., Japan). Also, among proteases extracted from particular types of thermophilic bacteria, some have been known to enhance their activity at a NaCl concentration as high as 1-5 M (Inouye et al. J. Biochem 1997; 122, pp. 358-364).

However, nothing has been elucidated about the effect of NaCl on the activity of glycosyltransferases, regardless of their origin.

Patent Document 1: JP 10-234364 A
Non-patent Document 1: Cell Technology, Supplement, July 1996, pp. 104-107
Non-patent Document 2: J. Biochem 1997; 122, pp. 358-364

DISCLOSURE OF THE INVENTION

Problems to be Solved by the Invention

The problem to be solved by the present invention is to develop an inexpensive and simple method which allows efficient glycosylation with a glycosyltransferase when compared to conventional enzymatic reaction systems.

Means for Solving the Problems

As a result of extensive and intensive efforts made to solve the problem stated above, the inventors of the present invention have found that glycosyltransferases derived from microorganisms belonging to the Vibrionaceae enhance their enzymatic activity when an appropriate amount of NaCl is added to their enzymatic reaction.

The effect of the present invention is specific to Na ions and cannot be provided by other monovalent ions such as K or divalent ions such as $Mg^{2+}$. Moreover, the Na ion-induced activity increase in the present invention is an effect unique to glycosyltransferases derived from microorganisms belonging to the Vibrionaceae and is not observed in glycosyltransferases derived from other organisms (e.g., mammals) at the time of the present invention.

Thus, the present invention relates to a method for increasing the enzymatic activity of glycosyltransferases derived from microorganisms belonging to the Vibrionaceae, which comprises adding an appropriate amount of NaCl to their enzymatic reaction systems.

Glycosyltransferases derived from microorganisms belonging to the Vibrionaceae can be expected to enhance their enzyme activity when NaCl is added by the method of the present invention. Alternatively, those skilled in the art who review the disclosures of this specification will easily confirm the increase in enzyme activity induced by addition of NaCl to the reaction system.

In the method of the present invention, examples of microorganisms belonging to the Vibrionaceae include, but are not limited to, microorganisms of the genus *Vibrio, Photobacterium, Allomonas, Catenococcus, Enterovibrio* or *Salinivibrio*. Among microorganisms belonging to the Vibrionaceae, preferred are those belonging to the genus *Photobacterium* or those belonging to the genus *Vibrio*. Examples of microorganisms belonging to the genus *Photobacterium* include, but are not limited to, *Photobacterium damselae; Photobacterium phosphoreum, Photobacterium angustum, Photobacterium indicum, Photobacterium iliopiscarium, Photobacterium profundum, Photobacterium leiognathi* or other *Photobacterium* spp. Likewise, examples of microorganisms belonging to the genus *Vibrio* include, but are not limited to, *Vibrio fisheri, Vibrio aerogenes, Vibrio calviensis, Vibrio rumoiensis, Vibrio salmonicida, Vibrio cholerae, Vibrio alginolyticus, Vibrio vulnificus* or other *Vibrio* spp.

The microorganisms of the Vibrionaceae in the present invention are preferably, but not limited to, marine microorganisms. Marine microorganisms refer to, for example, microorganisms obtainable from sea water, sea sand, fish, shell, etc.

Among glycosyltransferases derived from microorganisms of the Vibrionaceae, preferred are sialyltransferases. An example is β-galactoside-α2,6-sialyltransferase disclosed in JP 10-234364 A. Alternatively, β-galactoside-α2,3-sialyltransferases derived from microorganisms belonging to the Vibrionaceae may also be possible.

β-Galactoside-α2,3-sialyltransferases derived from microorganisms belonging to the Vibrionaceae were identified by the inventors of the present invention. International patent applications were filed for these enzymes under PCT/JP2005/007340 (filed on Apr. 15, 2005) and PCT/JP2005/010814 (filed on Jun. 13, 2005), which are hereby incorporated by reference. Detailed procedures and results for identification and preparation of these enzymes are also shown later in the reference examples.

As used herein, the term "glycosyltransferase" encompasses not only enzymes extracted from native materials, i.e., microorganisms belonging to the Vibrionaceae or their culture media, but also enzymes produced by genetic engineering in host cells other than microorganisms belonging to the Vibrionaceae which are the source of the enzymes. In terms of the degree of enzyme purification, this term is intended to encompass enzymes purified enough to show a single band in gel electrophoresis and crude enzymes with activity. Moreover, glycosyltransferases may be composed of the same polypeptides as the native enzymes, or may be composed of polypeptides modified to contain active sites of the native enzymes.

In the method of the present invention, conditions for enzymatic reaction are not limited in any way as long as they allow the glycosyltransferases to react. The enzymatic reaction solution used may be, but not limited to, a buffer such as acetate buffer, cacodylate buffer, phosphate buffer or Bis-Tris buffer. The pH and/or reaction temperature for the reaction solution are not limited in any way as long as they allow each glycosyltransferase to react, and preferred are the optimum pH and/or optimum temperature for each glycosyltransferase. Conditions of glycosyl donor and glycosyl acceptor concentrations are not limited in any way as long as they allow glycosyltransferases to react, and those skilled in the art can determine these concentrations as appropriate.

In the method of the present invention, the timing of NaCl addition to the reaction system for glycosyltransferase is not limited in any way. For example, NaCl may be dissolved in an enzymatic reaction buffer, an enzyme solution, a glycosyl acceptor substrate solution or a glycosyl donor solution before use in the enzymatic reaction, or alternatively, a NaCl solution may be prepared at an appropriate concentration and added to the reaction system independently of the above solutions. In such an embodiment where a NaCl solution is prepared independently of enzymatic reaction components, NaCl may be added to the reaction system either immediately before or during the reaction.

In all cases, the amount of NaCl added in the method of the present invention is 0.1 M to 2.0 M, preferably 0.1 M to 1.5 M, and more preferably 0.2 M to 1.0 M, based on the total volume of the reaction.

In the method of the present invention, examples of acceptors available for use include, but are not limited to, monosaccharides, disaccharides, polysaccharides, glycopeptides, glycoproteins and glycolipids.

In the method of the present invention, examples of glycosyl donors available for use include, but are not limited to, sugar nucleotides such as CMP-sialic acid (e.g., CMP-NeuAc, CMP-KDN, CMP-NeuGc), UDP-galactose, GDP-fucose, GDP-mannose, UDP-N-acetylglucosamine, UDP-N-acetylgalactosamine and UDP-glucose.

As used herein, the term "glycosyltransferase" refers to an enzyme that catalyzes the transfer of a glycosyl group from a glycosyl-containing glycosyl donor to a glycosyl acceptor. Examples of glycosyltransferases include, but are not limited to, sialyltransferases that catalyze sialic acid transfer, glucosyltransferases that catalyze glucose transfer, galactosyltransferases that catalyze galactose transfer, acetylgalactosaminyltransferases that catalyze N-acetylgalactosamine transfer, acetylglucosaminyltransferases that catalyze N-acetylglucosamine transfer, mannosyltransferases that catalyze mannose transfer, and fucosyltransferases that catalyze fucose transfer.

As used herein, the term "sialyltransferase" refers to an enzyme that catalyzes the transfer of sialic acid from a sialic acid-containing glycosyl donor to a glycosyl acceptor. Examples of sialyltransferases in the method of the present invention include, but are not limited to, galactoside-α2,3-sialyltransferase, galactoside-α2,4-sialyltransferase, galactoside-α2,6-sialyltransferase, sialate-α2,8-sialyltransferase and sialate-α2,9-sialyltransferase. In a preferred embodiment, sialyltransferase in the method of the present invention is galactoside-α2,6-sialyltransferase and/or galactoside-α2,3-sialyltransferase.

As used herein, the term "β-galactoside-α2,6-sialyltransferase" is intended to mean a protein having the ability to transfer sialic acid from cytidine monophosphate (CMP)-sialic acid to the 6-position of a monosaccharide (e.g., a galactose residue) which is a constituting member of complex carbohydrate sugar chains or free sugar chains and has a hydroxyl group on the carbon at the 6-position, to the 6-position of a monosaccharide (e.g., a galactose residue) which is a constituting member of oligosaccharides such as lactose or N-acetylgactosamine and has a hydroxyl group on the carbon at the 6-position, or to the 6-position of a monosaccharide (e.g., galactose, mannose, N-acetylglucosamine or N-acetylgalactosamine) which may be used as a constituting member of complex carbohydrates and has a hydroxyl group on the carbon at the 6-position. It should be noted that all monosaccharides may be in either α-configuration or β-configuration. As used herein, the term "β-galactoside-α2,6-sialyltransferase activity" is intended to mean the ability described above for β-galactoside-α2,6-sialyltransferase.

As used herein, the term "β-galactoside-α2,3-sialyltransferase" is intended to mean a protein having the ability to transfer sialic acid from cytidine monophosphate (CMP)-sialic acid to the 3-position of a monosaccharide (e.g., a galactose residue) which is a constituting member of complex carbohydrate sugar chains or free sugar chains and has a hydroxyl group on the carbon at the 3-position, to the 3-position of a monosaccharide which is a constituting member of oligosaccharides such as lactose or N-acetylgactosamine and has a hydroxyl group on the carbon at the 3-position, or to the 3-position of a monosaccharide (e.g., galactose, mannose, N-acetylglucosamine or N-acetylgalactosamine) which may be used as a constituting member of complex carbohydrates and has a hydroxyl group on the carbon at the 3-position. It should be noted that all monosaccharides may be in either α-configuration or β-configuration. As used herein, the term "β-galactoside-α2,3-sialyltransferase activity" is intended to mean the ability described above for β-galactoside-α2,3-sialyltransferase.

Likewise, the term "sialic acid" as used herein refers to a neuraminic acid derivative belonging to the sialic acid family, and more specifically refers to, but is not limited to, N-acetylneuraminic acid (Neu5Ac), N-glycolylneuraminic acid (Neu5Gc), 5-deamino-5-hydroxyneuraminic acid (KDN), disialic acid or the like.

The method of the present invention is a method for increasing the enzyme activity of glycosyltransferases derived from microorganisms belonging to the Vibrionaceae, which comprises adding NaCl to their enzyme reaction systems. As used herein, the phrase "increasing the enzyme activity" is intended to mean that the reaction efficiency is increased by carrying out the reaction in the presence of NaCl when compared to the absence of NaCl. In a preferred embodiment, the phrase "increasing the enzyme activity" is intended to mean that when the reaction is carried out in the presence of NaCl, the relative enzyme activity is 1-fold higher, more preferably 1.1-fold higher, and even more preferably 1.2-fold higher than in the absence of NaCl. The upper limit of increased enzyme activity may not be determined or may preferably be set to 10-fold or less, 5-fold or less, 3-fold or less, or 2-fold or less.

EXAMPLES

Figure 1:
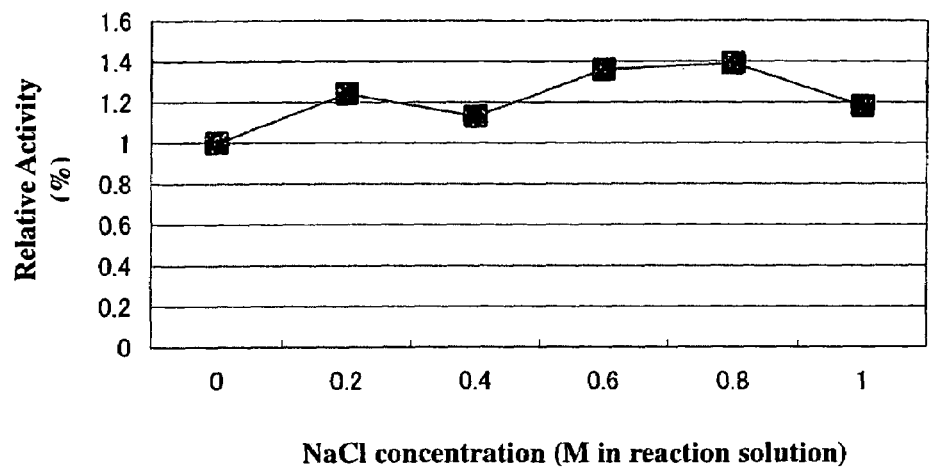
FIG. 1 is a graph showing the effect of NaCl on the enzyme activity of glycosyltransferase (α2,6-sialyltransferase; native) derived from a bacterium belonging to the genus Photobacterium (Photobacterium damselae).

The present invention will now be described in more detail by way of the following examples, which are not intended to limit the scope of the invention.

Reference Example 1

Identification and Cloning of α2,3-sialyltransferase Derived from Microorganisms of the Vibrionaceae Material and Method Reference Example 1-1

Screening and Strain Identification of Microorganisms Expressing α2,3-sialyltransferase Sea water, sea sand, sea mud, sea fish, or shell was used as an inoculation source. This inoculation source was applied onto agar plates containing marine broth agar 2216 medium (Becton Dickinson) to obtain microorganisms growing at 15° C., 25° C. or 30° C. After the resulting microorganisms were pure-cultured in a routine manner, each microorganism was cultured using a liquid medium composed of marine broth 2216 medium (Becton Dickinson). After the microorganisms were fully grown, the cells were collected from each culture solution by centrifugation. To the collected cells, 20 mM cacodylate buffer (pH 6.0) containing 0.2% Triton X-100 (Kanto Kagaku, Japan) was added, and the cells were suspended therein. This cell suspension was ultrasonicated under ice cooling to homogenize the cells. This cell homogenate was used as an enzyme solution and measured for its sialyltransferase activity, and further determined for its binding mode of sialic acid using a pyridylaminated sugar chain. As a result, strains having α2,3-sialyltransferase activity, i.e., JT-ISH-467, JT-ISH-224 and JT-FAJ-16 were obtained. Incidentally, the JT-ISH-467 strain was obtained from the epidermis of Japanese common squid, the JT-ISH-224 strain was obtained from the internal organs of barracuda, and the JT-FAJ-16 strain was obtained from the internal organs of horse mackerel.

Sialyltransferase activity was measured as described in J. Biochem., 120, pp. 104-110 (1996) (which is hereby incorporated by reference in its entirety). More specifically, the enzyme reaction was accomplished by using CMP-NeuAc (70 nmol, containing 25000 cpm CMP-NeuAc in which NeuAc was labeled with $^{14}$C, 356 cpm/nmol) as a glycosyl donor substrate, lactose (1.25 μmol) as a glycosyl acceptor substrate, and the enzyme-containing reaction solution (30 μl) prepared as described above. The enzymatic reaction was carried out at 25° C. for 10 to 30 minutes. After completion of the reaction, 1.97 ml of 5 mM phosphate buffer (pH 6.8) was added to the reaction solution, which was then applied to a Dowex 1×8 ($PO_4^{3-}$ form, 0.2×2 cm, BIO-RAD) column. The radioactivity was measured for the reaction product, i.e., sialyllactose contained in the eluate (0 to 2 ml) from this column to calculate the enzyme activity.

Determination of the binding mode of sialic acid was accomplished by using a pyridylaminated sugar chain. The resulting enzyme was used to carry out an enzymatic reaction in the presence of a pyridylaminated sugar chain as a glycosyl acceptor substrate. The pyridylaminated sugar chain used for analysis was pyridylaminated lactose (Galβ1, 4Glc-PA, PA-Sugar Chain 026, Takara Bio Inc., Japan). As a standard, pyridylaminated α2,3sialyllactose (NeuAcα2,3Galβ1, 4Glc-PA, PA-Sugar Chain 029, Takara Bio Inc., Japan) was used. The glycosyl acceptor substrate, CMP-NeuAc and the enzyme were dissolved at 2.0 μM, 5.7 μM and about 20 mU/ml, respectively, in 25 μl of 20 mM cacodylate buffer (pH 6.0) or Bis-Tris buffer (pH 6.0), and then reacted at 25° C. for 3 to 18 hours. After completion of the reaction, the reaction solution was treated at 100° C. for 2 minutes to deactivate the enzyme, followed by HPLC to analyze the reaction product.

The HPLC system used was, Shimadzu LC10A (Shimadzu Corporation, Japan) and the analytical column used was Takara PALPAK Type R (Takara Bio Inc., Japan). The column which had been equilibrated with 100 mM acetate-triethylamine (pH 5.0) containing 0.15% N-butanol was injected with the reaction solution diluted with Eluent A (100 mM acetate-triethylamine, pH 5.0). For elution of the pyridylaminated sugar chain, Eluent A (100 mM acetate-triethylamine, pH 5.0) and Eluent B (100 mM acetate-triethylamine containing 0.5% n-butanol, pH 5.0) were used to successively elute the pyridylaminated sugar chain with a linear gradient of 30% to 100% Eluent B (0 to 35 minutes) and then 100% Eluent B (35 to 50 minutes). The analysis was performed under the following conditions: flow rate: 1 ml/min, column temperature: 40° C., detection: fluorescence (Ex: 320 nm, Em: 400 nm).

(i) JT-ISH-467 Strain

The resulting JT-ISH-467 strain was found to have the following properties:

(Microbiological Properties)
(1) The cells are in bacillary form and have a size of 0.7 to 0.8 μm×1.5 to 2.0 μm.
(2) Motility: −
(3) Gram staining: −
(4) Spore: −

(Physiological and Biochemical Properties)
(1) Growth temperature: + at 4° C., + at 25° C., − at 30° C.
(2) Colony color: not producing characteristic colony pigment
(3) O/F test: +/−
(4) Catalase test: −
(5) Oxidase test: +
(6) Acid production from glucose: −
(7) Gas generation from glucose: −
(8) Photogenesis: +
(9) Reduction of nitrate: +
(10) Indole formation: +
(11) Glucose acidification: −
(12) Arginine dihydrolase: +
(13) Urease: −
(14) Esculin hydrolysis: −
(15) Gelatin hydrolysis: −
(16) β-Galactosidase: +
(17) Glucose assimilation: −
(18) L-Arabinose assimilation: −
(19) D-Mannose assimilation: −
(20) D-Mannitol assimilation: −
(21) N-Acetyl-D-glucosamine assimilation: −
(22) Maltose assimilation: −
(23) Potassium gluconate assimilation: −
(24) n-Capric acid assimilation: −
(25) Adipic acid assimilation: −
(26) dl-Malic acid assimilation: −
(27) Sodium citrate assimilation: −
(28) Phenyl acetate assimilation: −
(29) Cytochrome oxidase: +
(30) GC content of DNA isolated from bacterial cells (mol %): 39.7%

(Nucleotide Sequence Analysis of 16S rRNA Gene and Species Identification Based on DNA-DNA Hybridization)

The genomic DNA extracted from the JT-ISH-467 strain in a routine manner was used as a template for PCR to amplify the entire nucleotide sequence of the 16S rRNA gene, thereby determining its nucleotide sequence. The nucleotide sequence is shown in SEQ ID NO: 3. This nucleotide sequence showed homology as high as 100% with the nucleotide sequence of the 16S rRNA gene in *Photobacterium phosphoreum* the type strain ATCC11040. This result indicated that the JT-ISH-467 strain belongs to the genus *Photobacterium*. However, since the 16S rRNA gene is merely a part of the whole bacterial genome, identification analysis based on the nucleotide sequence of the 16S rRNA gene is recognized as producing a very large error for the distance between very closely related organisms at species level. For this reason, DNA-DNA hybridization testing, which is commonly used for quantitative evaluation of the relatedness among strains within the same genus, was used for species determination. Total DNAs of the JT-ISH-467 strain and *Photobacterium phosphoreum* the type strain NCIMB1282 (which is the same strain as ATCC11040) were extracted and tested. As a result, a homology level (DNA-DNA relatedness) as high as 84.7% was obtained. Since DNA-DNA homology between the same species is usually 60% or more, the JT-ISH-467 strain was identified to be *Photobacterium phosphoreum*. DNA-DNA hybridization testing was accomplished by photobiotin labeling using microplates, as described in "Experimental Procedures for Classification and Identification of Microorganisms" (edited by Kenichiro Suzuki, Akira Hiraishi and Akira Yokota, Springer-Verlag, Tokyo, September 2001, hereby incorporated by reference in its entirety).

(ii) JT-ISH-224 Strain

The resulting JT-ISH-224 strain was found to have the following properties:

(Microbiological Properties)
(1) The cells are in bacillary form and have a size of 0.7 to 0.8 μm×1.0 to 1.5 μm.
(2) Motility: +
(3) Gram staining: −
(4) Spore: −

(Physiological and Biochemical Properties)
 (1) Growth temperature: − at 4° C., + at 25° C., + at 30° C., − at 37° C.
 (2) Colony color: not producing characteristic colony pigment
 (3) O/F test: +/−
 (4) Catalase test: +
 (5) Oxidase test: +
 (6) Acid production from glucose: +
 (7) Gas generation from glucose: +
 (8) Photogenesis: −
 (9) Reduction of nitrate: +
 (10) Indole formation: +
 (11) Glucose acidification: −
 (12) Arginine dihydrolase: +
 (13) Urease: −
 (14) Esculin hydrolysis: −
 (15) Gelatin hydrolysis: −
 (16) β-Galactosidase: +
 (17) Glucose assimilation: −
 (18) L-Arabinose assimilation: −
 (19) D-Mannose assimilation: −
 (20) D-Mannitol assimilation: −
 (21) N-Acetyl-D-glucosamine assimilation: −
 (22) Maltose assimilation: −
 (23) Potassium gluconate assimilation: −
 (24) n-Capric acid assimilation: −
 (25) Adipic acid assimilation: −
 (26) dl-Malic acid assimilation: −
 (27) Sodium citrate assimilation: −
 (28) Phenyl acetate assimilation: −
 (29) Cytochrome oxidase: +
 (30) O/129 sensitivity: 10 μg −, 15 μg +
 (31) GC content of DNA isolated from bacterial cells (mol %): 39.4%

(Nucleotide Sequence Analysis of 16S rRNA Gene)
 The genomic DNA extracted from the JT-ISH-224 strain in a routine manner was used as a template for PCR to amplify the entire nucleotide sequence of the 16S rRNA gene, thereby determining its nucleotide sequence. The nucleotide sequence is shown in SEQ ID NO: 32.
 The JT-ISH-224 strain was shown to belong to the Vibrionaceae, based on its morphological observations including growth on marine agar, bacillary form, Gram staining, fermentative glucose degradation and O/129 sensitivity, along with the results from the physiological and biochemical property tests. Moreover, the DNA nucleotide sequence of the 16S rRNA gene in the JT-ISH-224 strain was found to share the highest homology (99.2%) with the sequence of the 16S rRNA gene in *Photobacterium phosphoreum* the type strain ATCC11040, and the second highest homology (99.1%) with the sequence of the 16S rRNA gene in *Photobacterium iliopiscarium* the type strain ATCC51760. These results indicated that the JT-ISH-224 strain is a microorganism belonging to the genus *Photobacterium* (*Photobacterium* sp.).

(iii) JT-FAJ-16 Strain
 The resulting JT-FAJ-16 strain was found to have the following properties:

(Microbiological Properties)
 (1) The cells are in bacillary form and have a size of 0.7 to 0.8 μm×1.2 to 1.5 μm.
 (2) Motility: −
 (3) Gram staining: −
 (4) Spore: −

(Physiological and Biochemical Properties)
 (1) Growth temperature: + w at 4° C., + at 25° C., + at 30° C., + at 37° C.
 (2) Colony color: light-yellow to cream
 (3) O/F test: +/+
 (4) Catalase test: +
 (5) Oxidase test: +
 (6) Acid production from glucose: +
 (7) Gas generation from glucose: −
 (8) Reduction of nitrate: +
 (9) Indole formation: −
 (10) Glucose acidification: +
 (11) Arginine dihydrolase: −
 (12) Urease: −
 (13) Esculin hydrolysis: +
 (14) Gelatin hydrolysis: −
 (15) β-Galactosidase: +
 (16) Glucose assimilation: −
 (17) L-Arabinose assimilation: −
 (18) D-Mannose assimilation: −
 (19) D-Mannitol assimilation: −
 (20) N-Acetyl-D-glucosamine assimilation: −
 (21) Maltose assimilation: −
 (22) Potassium gluconate assimilation: −
 (23) n-Capric acid assimilation: −
 (24) Adipic acid assimilation: −
 (25) dl-Malic acid assimilation: −
 (26) Sodium citrate assimilation: −
 (27) Phenyl acetate assimilation: −
 (28) Cytochrome oxidase: +
 (29) O/129 sensitivity: −
 (30) Mannitol fermentation: +
 (31) Inositol fermentation: +
 (32) Arabinose fermentation: +
 (33) Rhamnose fermentation: −
 (34) Saccharose fermentation: −
 (35) Growth in NaCl: 3% NaCl+, 4% NaCl+, 6% NaCl+
 (36) Starch hydrolysis: −
 (37) Tween 80 decomposition: −
 (38) $H_2S$ formation: −
 (39) Acetoin formation (VP test): −

(Nucleotide Sequence Analysis of 16S rRNA Gene)
 The genomic DNA extracted from the JT-FAJ-16 strain in a routine manner was used as a template for PCR to amplify the entire nucleotide sequence of the 16S rRNA gene, thereby determining its nucleotide sequence. The nucleotide sequence is shown in SEQ ID NO: 33.
 The JT-FAJ-16 strain was shown to belong to the Vibrionaceae, based on its morphological observations including growth on marine agar, bacillary form, Gram staining, fermentative glucose degradation and O/129 sensitivity, along with the results from the physiological and biochemical property tests. Moreover, the DNA nucleotide sequence of the 16S rRNA gene in the JT-FAJ-16 strain was found to share the highest homology (99.5%) with the sequence of the 16S rRNA gene in a *Vibrio rumoiensis* the type strain. These results indicated that the JT-FAJ-16 strain is a microorganism belonging to the genus *Vibrio* (*Vibrio* sp.).

Reference Example 1-2

Extraction and Purification of α2,3-sialyltransferase from *Photobacterium phosphoreum* JT-ISH-467

From colonies of *Photobacterium phosphoreum* strain JT-ISH-467 subcultured on marine agar 2216 plates, the cells were collected with a loop, inoculated into 10 ml marine broth 2216 liquid medium and cultured with shaking at 25° C. at 180 rpm for 8 hours.

Main culturing was accomplished in the following manner. Marine broth 2216 medium (300 ml) supplemented with 20 g/L Bacto Peptone and 4 g/L Bacto Yeast Extract was charged into a 1000 ml baffle flask and sterilized in an autoclave (121° C., 15 minutes). The same medium was prepared in 36 flasks (10.8 L in total). Each flask was inoculated with the above culture solution (10 ml) and cultured with shaking at 25° C. at 180 rpm for 24 hours. The cultured medium was centrifuged to collect the cells (about 60 g on a wet weight basis).

These cells were suspended in 990 ml of 20 mM cacodylate buffer (pH 6.0) containing 0.2% Triton X-100 and 3 M sodium chloride, and ultrasonically homogenized under ice cooling. The cell homogenate was centrifuged at 4° C. at 100,000×g for 1 hour to obtain the supernatant. The resulting supernatant was introduced into a dialysis membrane tube and dialyzed at 4° C. against 20 mM cacodylate buffer (pH 6.0) containing 0.2% Triton X-100 until sodium chloride was reduced to around 20 mM. Since precipitates were generated in the solution after dialysis, centrifugation was performed at 4° C. at 100,000×g for 1 hour to remove the precipitates.

This crude enzyme solution was loaded to an anion exchange column called HiPrep 16/10 DEAE FF (Amersham Biosciences), which had been equilibrated with 20 mM cacodylate buffer (pH 6.0) containing 0.2% Triton X-100 (surfactant). The column was eluted with a linear gradient up to 1 M sodium chloride in 20 mM cacodylate buffer (pH 6.0) containing 0.2% Triton X-100 to thereby collect an enzymatically active fraction eluted at around 0.25 M sodium chloride concentration.

The collected fraction was diluted with 20 mM phosphate buffer (pH 6.0) and loaded to hydroxyapatite (Bio-Rad) which had been equilibrated with 20 mM phosphate buffer (pH 6.0) containing 0.2% Triton X-100, followed by elution with a linear gradient from 20 mM phosphate buffer (pH 6.0) containing 0.2% Triton X-100 to 500 mM phosphate buffer (pH 6.0) containing 0.2% Triton X-100 to thereby collect an enzymatically active fraction eluted at around 125 mM phosphate buffer concentration.

This fraction was loaded to a MonoQ 5/50 GL (Amersham Biosciences) anion exchange column. The column was eluted with a linear gradient up to 1 M sodium chloride in 20 mM cacodylate buffer (pH 6.0) containing 0.2% Triton X-100 to thereby collect an enzymatically active fraction eluted at around 300 mM sodium chloride concentration.

This fraction was diluted 10-fold with 20 mM cacodylate buffer (pH 7.0) containing 0.2% Triton X-100 and loaded to a MonoQ 5/50 GL (Pharmacia) anion exchange column. The column was eluted with a linear gradient up to 1 M sodium chloride in 20 mM cacodylate buffer (pH 7.0) containing 0.2% Triton X-100 to thereby collect an enzymatically active fraction eluted at around 300 mM sodium chloride concentration.

This fraction was diluted 2-fold with 20 mM cacodylate buffer (pH 7.0) containing 0.2% Triton X-100 and 0.2 M sodium chloride, and then fractionated on a HiLoad 16/60 Superdex 200 prep grade (Amersham Biosciences) gel filtration column. The column was eluted with 20 mM cacodylate buffer (pH 7.0) containing 0.2% Triton X-100 and 0.2 M sodium chloride.

The active fraction was electrophoresed on an SDS-polyacrylamide gel (the concentration of the acrylamide gel: 12.5%), indicating that the target enzyme showed a single band with a molecular weight of about 39,000 (herein referred to as "467 native"). The specific activity of this fraction was about 350-fold higher than that of the cell homogenate (Table 3).

As to purification of α2,3-sialyltransferase derived from the JT-ISH-467 strain from a crude enzyme solution, Table 1 shows the enzyme activity of the sample after each of the purification steps mentioned above. The enzyme activity was measured by the method reported in J. Biochem. 120, pp. 104-110 (1996), in the same manner as described in Example 7-1. For protein quantification, a Coomassie Protein Assay Reagent (PIERCE) was used according to the instruction manual attached thereto. One enzyme unit (1 U) was defined as the amount of enzyme required to transfer 1 micromole of sialic acid per minute.

TABLE 1

Purification of α2,3-sialyltransferase derived from JT-ISH-467 strain from crude enzyme solution

| Purification step | Volume (ml) | Total protein (mg) | Total activity (U) | Specific activity (U/mg) | Yield (%) | Purification degree (fold) |
| --- | --- | --- | --- | --- | --- | --- |
| Crude enzyme solution | 950 | 2,930 | 21.3 | 0.0073 | 100 | 1 |
| DEAE | 90 | 468 | 4.0 | 0.0085 | 19 | 1.2 |
| Hydroxyapatite | 85 | 129 | 2.7 | 0.0212 | 13 | 2.9 |
| Mono Q (pH 6) | 1 | 1.64 | 0.073 | 0.0448 | 0.34 | 6.2 |
| Mono Q (pH 7) | 0.5 | 0.138 | 0.023 | 0.164 | 0.11 | 22.5 |
| Superdex 200 | 1.5 | 0.0047 | 0.012 | 2.50 | 0.044 | 343.6 |

Reference Example 1-3

Determination of Binding Mode of Sialic Acid Using Pyridylaminated Sugar Chain

Using the enzyme obtained in Reference Example 1-2, the enzyme reaction was carried out as described in Reference Example 1-1 using a pyridylaminated sugar chain as a glycosyl acceptor substrate. The results indicated that pyridylaminated α2,3-sialyllactose was synthesized from pyridylaminated lactose when using this enzyme.

Reference Example 1-4

Nucleotide Sequence Analysis and Transformation of Gene Encoding α2,3-sialyltransferase Produced by *Photobacterium phosphoreum* Strain JT-ISH-467

(1) Purification of Genomic DNA and Creation of Genomic Library

From a cell pellet of the JT-ISH-467 strain (about 0.5 g), genomic DNA (about 100 μg) was prepared using a Qiagen Genomic-tip 100/G (Qiagen) in accordance with the instructions attached to the kit. Relative to 1-2 μg of DNA, 0.1 to 0.2 units of Sau3AI, having a four-letter recognition sequence, was reacted to partially digest the DNA. The reaction buffer used was one attached to the enzyme and the reaction conditions were set at 37° C. for 30 minutes. After completion of the reaction, EDTA (pH 8.0) was added at a final concentration of 25 mM to the reaction solution, followed by phenol-chloroform treatment. The genomic DNA was collected by ethanol precipitation and dissolved in 400 μl TE. In a centrifugal tube (Hitachi 40PA), a 40-10% gradient was prepared from 40% sucrose buffer (20 mM Tris pH 8.0, 5 mM EDTA pH 8.0, 1 M NaCl) and 10% sucrose buffer using a gradient preparation unit, and the above partially-digested DNA solution was overlayed thereon. Using an ultracentrifuge (Hitachi SCP70H, rotor: SRP28SA), the tube was centrifuged at 26,000 rpm at 20° C. for 15 hours. After centrifugation, a hole was made with a 25 G needle at the bottom of the tube to collect 1 ml aliquots from the solution at the bottom. Using a submarine electrophoretic chamber, a part of each collected sample containing the genomic DNA was electrophoresed on a 0.5-0.6% agarose gel/TAE buffer at 26 V for 20 hours to observe a fraction containing DNA of 9-16 kb size. As a marker, λ/HindIII was used. After addition of 2.5 ml TE to reduce the sucrose concentration, the fraction containing the DNA fragment of 9-16 kb size was ethanol precipitated, rinsed and dissolved in a small volume of TE.

λDASH II (Stratagene) was used as a vector to create a genomic library of the JT-ISH-467 strain. Ligation between the λDASH II/BamHI vector and the genomic DNA fragment was performed overnight at 12° C. using a Stratagene ligation kit. After the reaction, the reaction solution was reacted with GigaPack III Gold Packaging extract, whereby the λ vector carrying the genomic DNA was incorporated into phage particles. The phage solution was stored at 4° C. in 500 μl SM buffer and 20 μl chloroform. *E. coli* XL1-Blue MRA(P2) (Stratagene) was grown in LBMM (LB+0.2% maltose+10 mM MgSO$_4$) to A$_{600}$=0.5, and 200 μl of this culture solution was incubated with an appropriate amount of the phage solution at 37° C. for 15 minutes. This solution was mixed with 4 ml NZY top agarose kept at 48° C., and plated in a NZY agar plate (a plastic dish of 9 cm diameter). The plate was cultured overnight at 37° C. and the number of plaques was counted to calculate the titer. As a result, the library size was calculated to be about 300,000 pfu (plaque forming unit).

(2) Primer Design and Probe Preparation

A Procise 494 cLC Protein Sequencing System (Applied Biosystems) was used to determine the amino-terminal (N-terminal) amino acid sequence and internal amino acid sequences of β-galactoside-α2,3-sialyltransferase derived from the JT-ISH-467 strain.

Determination of the N-terminal amino acid sequence was accomplished as follows. The sialyltransferase was subjected to SDS-polyacrylamide gel electrophoresis on a 5/20% gradient gel (ATTO). After electrophoresis, the enzyme was adsorbed onto a PVDF membrane, and the sequence of amino-terminal 10 amino acids was determined with an amino acid sequencer. As a result, the N-terminal amino acid sequence of this enzyme was XNSDSKHNNS (SEQ ID NO: 4).

Also, determination of internal amino acid sequences was accomplished as follows. The sialyltransferase was subjected to SDS-polyacrylamide gel electrophoresis on a 5/20% gradient gel (ATTO). After staining the gel, a band of interest was excised and treated at 35° C. for 20 hours in lysyl endopeptidase-containing Tris buffer (pH 8.5). Then, the entire solution was applied to reversed-phase HPLC (column: Symmetry C18 3.5 μm) to separate fragment peptides. Analysis with an amino acid sequencer indicated that internal amino acid sequences of this enzyme had the following sequences:

```
SLDSMILTNEIK,            (SEQ ID NO: 5)

FYNFTGFNPE               (SEQ ID NO: 6)
and

GHPSATYNQQIIDAHNMIEIY.   (SEQ ID NO: 7)
```

Based on the thus determined partial amino acid sequences of α2,3-sialyltransferase derived from *Photobacterium phosphoreum* JT-ISH-467, i.e., the N-terminal amino acid sequence XNSDSKHNNS (SEQ ID NO: 4) and two of the three internal amino acid sequences: FYNFTGFNPE (SEQ ID NO: 6) and GHPSATYNQQIIDAHNMIEIY (SEQ ID NO: 7), the following degenerate primers were designed and synthesized. Namely, the three primers shown in Table 2 below were synthesized from the N-terminal amino acid sequence XNSDSKHNNS (SEQ ID NO: 4).

TABLE 2

| Name | Sequence 5'-3' | Mix rate | Length |
|---|---|---|---|
| 467N-RV | AAY WSI GAY WSI AAR CAY AAY AA (SEQ ID NO: 8) | 256 | 23mer |
| 467N-RV2 | GAY WSI AAR CAY AAY AAY WS (SEQ ID NO: 9) | 512 | 20mer |
| 467N-RV3 | AAY WSN GAY WSI AAR CAY AAY AA (SEQ ID NO: 10) | 1024 | 23mer |

In the table, Y represents thymine or cytosine; W represents thymine or adenine; S represents cytosine or guanine; R represents adenine or guanine; N represents adenine, guanine, cytosine or thymine; and I represents inosine.

Also, the four primers shown in Table 3 below were synthesized from the internal amino acid sequence GHPSATYNQQIIDAHNMIEIY (SEQ ID NO: 7).

TABLE 3

| Name | Sequence 5'-3' | Mix rate | Length |
|---|---|---|---|
| 467in1RV | ATH ATH GAY GCN CAY AAY ATG (SEQ ID NO: 11) | 288 | 21mer |
| 467in1FW | CAT RTT RTG NGC RTC DAT DAT (SEQ ID NO: 12) | 288 | 21mer |
| 467in1RV2 | TAY AAY CAR CAR ATH ATH GAY GC (SEQ ID NO: 13) | 288 | 23mer |
| 467in1FW2 | GCR TCD ATD ATY TGY TGR TTR TA (SEQ ID NO: 14) | 288 | 23mer |

In the table, H represents thymine, cytosine or adenine; Y represents thymine or cytosine; R represents adenine or guanine; D represents adenine, guanine or thymine; and N represents adenine, guanine, cytosine or thymine.

Moreover, the two primers shown in Table 4 below were synthesized from the internal amino acid sequence FYNFTGFNPE (SEQ ID NO: 6).

TABLE 4

| Name | Sequence 5'-3' | Mix rate | Length |
|---|---|---|---|
| 467in2RV (SEQ ID NO: 15) | TAY AAY TTY ACN GGN TTY AAY CC | 512 | 23mer |
| 467in2FW (SEQ ID NO: 16) | GGR TTR AAN CCN GTR AAR TTR TA | 512 | 23mer |

In the table, Y represents thymine or cytosine; R represents adenine or guanine; and N represents adenine, guanine, cytosine or thymine.

These primers were used for PCR, in which the JT-ISH-467 strain genomic DNA extracted and purified in (1) above was used as a template, to amplify partial-length DNA of the JT-ISH-467-derived α2,3-sialyltransferase gene, which served as a probe for library screening. As to primer combinations, the following 13 combinations in total were used: 9 combinations of the three N-terminal sequence-derived primers with 467in1FW (SEQ ID NO: 12), 467in1FW2 (SEQ ID NO: 14) or 467 in2FW (SEQ ID NO: 16); 2 combinations of 467in1RV (SEQ ID NO: 11) or 467in1RV2 (SEQ ID NO: 13) with 467 in2FW (SEQ ID NO: 16); and 2 combinations of 467 in2RV (SEQ ID NO: 15) with 467in1FW (SEQ ID NO: 12) or 467in1FW2 (SEQ ID NO: 14). Each PCR reaction was carried out in 50 μl reaction solution containing 250 ng genomic DNA, 5 μl 10×Ex taq buffer, 4 μl 2.5 mM dNTPs, 5 pmol primer for each sequence and 0.5 μl Ex taq (Takara Bio Inc., Japan), using a Program Temp Control System PC-700 (ASTEK) under the following conditions: 96° C. for 3 minutes, (96° C. for 1 minute, 50° C. for 1 minute, 72° C. for 2 minutes)×40 cycles, and 72° C. for 6 minutes. As a result, amplification of PCR products was observed in 9 primer combinations (i.e., except for 467N-RV (SEQ ID NO: 8) & 467in1FW (SEQ ID NO: 12), 467N-RV (SEQ ID NO: 8) & 467 in2FW (SEQ ID NO: 16), 467in1RV (SEQ ID NO: 11) & 467 in2FW (SEQ ID NO: 16), and 467 in2RV (SEQ ID NO: 15) & 467in1FW (SEQ ID NO: 12)). Among these PCR products, one derived from the combination 467N-RV3 (SEQ ID NO: 10) & 467in1FW (SEQ ID NO: 12) which allowed specific and high-efficiency amplification was cloned into vector pCR2.1TOPO (Invitrogen). Ligation was carried out according to the instructions attached to the vector kit. The DNA was introduced into E. coli TB1 by electroporation and the plasmid DNA was extracted in a routine manner (Sambrook et al. 1989, Molecular Cloning, A laboratory manual, $2^{nd}$ edition (which is hereby incorporated by reference in its entirety)). This clone was analyzed by PCR with M13 primers (Takara Bio Inc., Japan) to determine the nucleotide sequence of the PCR product from both ends using an ABI PRISM fluorescent sequencer (Model 310 Genetic Analyzer, Perkin Elmer).

A homology search with the BLAST program was made for the determined DNA nucleotide sequence (929 bp: SEQ ID NO: 17) against the GeneBank database of the National Center for Biotechnology Information (NCBI). As a result, there was no DNA sequence with significant homology. This means that the DNA nucleotide sequence identified by the present invention for the α2,3-sialyltransferase gene derived from *Photobacterium phosphoreum* strain JT-ISH-467 is a novel sequence. Next, this nucleotide sequence was translated into amino acids and subjected again to a BLAST search, detecting 30% homology with α2,6-sialyltransferase (JC5898) from *Photobacterium damselae*, 26% homology with a putative protein PM0188 (AAK02272) of *Pasteurella multocida* subsp. *multocida* strain Pm70, and 21% homology with a putative protein HD0053 (AAP95068) of *Haemophilus ducreyi* strain 35000HP. Moreover, the translated amino acid sequence was found to contain the whole of the above internal amino acid sequences FYNFTGFNPE (SEQ ID NO: 6) and SLDSMILTNAIK (SEQ ID NO: 5) determined directly from the purified enzyme, as well as parts of the N-terminal amino acid sequence XNSDSKHNNS (SEQ ID NO: 4) and the internal amino acid sequence GHPSATYN-QQIIDAHNMIEIY (SEQ ID NO: 7). These results indicated that the cloned DNA was a part of the α2,3-sialyltransferase gene derived from *Photobacterium phosphoreum* strain JT-ISH-467, and that the amino acid sequence of α2,3-sialyltransferase derived from *Photobacterium phosphoreum* strain JT-ISH-467 according to the present invention was a novel amino acid sequence showing as low as 30% homology with the reported sequences.

(3) Screening and Gene Cloning

The DNA fragment cloned in (2) above, composed of a part of the α2,3-sialyltransferase gene derived from *Photobacterium phosphoreum* strain JT-ISH-467, was excised from the pCR2.1 TOPO vector with a restriction enzyme EcoRI and used as a probe to screen the *Photobacterium phosphoreum* strain JT-ISH-467-derived genomic DNA library created in (1) above. In a round dish of 9 cm diameter, about 300-500 pfu phages were plated together with XL1-blue MRA(P2) host cells according to the instructions attached to a λDASH II/BamHI vector kit (Stratagene). Plaques were contacted with a Hybond-N+ nylon membrane filter (Amersham), treated with alkali according to the instructions attached to the membrane to cause DNA denaturation, and then fixed on the membrane. The probe was labeled with $^{32}$P using a rediprime II™ DNA labelling system (Amersham Biosciences). Hybridization was carried out overnight at 65° C. in 0.5 M sodium phosphate buffer pH 7.2, 7% SDS, 1 mM EDTA, and washing conditions were set as follows: twice at 65° C. for 15 minutes in 40 mM sodium phosphate buffer pH 7.2, 1 mM EDTA, 5% SDS, followed by twice at 65° C. for 15 minutes in 40 mM sodium phosphate buffer pH 7.2, 1% SDS, 1 mM EDTA. During primary screening, 24 positive clones were obtained from about 5,000 pfu phages. Secondary screening (also serving as plaque purification) was performed on 18 of the resulting clones. As a result, it was possible to obtain 6 selected and purified plaques.

These plaques were collected, and each was plated in a NZY plate together with E. coli XL1-blue MRA(P2) at several ten thousand pfu per plate and incubated overnight at, 37° C. SM buffer was added in 4 ml volumes to 6 plates with confluent plaques, and the plates were allowed to stand overnight at 4° C. Phage plate lysates were collected with Pasteur pipettes, and λDNA was extracted and purified from each lysate with a QIAGEN Lambda Mini Kit (QIAGEN). These 6 λDNAs and the total genomic DNA of the JT-ISH-467 strain purified in (1) were digested with restriction enzymes EcoRI and HindIII, and fractionated by 0.7% agarose gel electrophoresis, followed by alkaline blotting with 0.4 M NaOH to transfer the gel onto a Hybond-N+ nylon membrane filter (Amersham Biosciences). Southern hybridization was performed on this filter, as described above, using the above 929 bp probe (SEQ ID NO: 17). As a result, EcoRI digestion detected a band of 9 kb or larger, while HindIII digestion detected a band of 4.6 kb for each λDNA and the genomic DNA. Then, each λDNA was digested again with HindIII and electrophoresed on an agarose gel to collect a 4.6 kb HindIII fragment, which was then cloned in a routine manner into a HindIII site of plasmid vector pBluescript SK(−).

Next, to determine the entire nucleotide sequence of the α2,3-sialyltransferase gene derived from *Photobacterium phosphoreum* strain JT-ISH-467, the primers shown in Table 5 below were synthesized on the basis of the partial DNA sequence of the gene (described above, 929 bp; SEQ ID NO: 17).

TABLE 5

| Name | Sequence 5'-3' | Length |
|---|---|---|
| 467-23STinRV1 | TGTTGATAGAGCAACATTACC (SEQ ID NO: 18) | 21mer |
| 467-23STinRV2 | TGGTAATACCTTATGGGCAG (SEQ ID NO: 19) | 20mer |
| 467-23STinRV3 | GAACAGCAACGGCAGAGC (SEQ ID NO: 20) | 18mer |
| 467-23STinRV4 | CTATTCAATTCAAGGATTGG (SEQ ID NO: 21) | 21mer |
| 467-23STinFW1 | TGGTAATGTTGCTCTATCAAC (SEQ ID NO: 22) | 21mer |
| 467-23STinFW2 | ACTGCCCATAAGGTATTACC (SEQ ID NO: 23) | 20mer |
| 467-23STinFW3 | GCTCTGCCGTTGCTGTTC (SEQ ID NO: 24) | 18mer |

Using these primers, the 4.6 kb HindIII fragment was analyzed for its internal nucleotide sequence with an ABI PRISM fluorescent sequencer (Model 310 Genetic Analyzer, Perkin Elmer) to analyze internal and surrounding nucleotide sequences of the α2,3-sialyltransferase gene derived from *Photobacterium phosphoreum* strain JT-ISH-467. As a result, the sequence of SEQ ID NO: 1 in the Sequence Listing was obtained. This sequence corresponds to the entire nucleotide sequence of the open reading frame (ORF) of the α2,3-sialyltransferase gene derived from *Photobacterium phosphoreum* strain JT-ISH-467. Since there is an in-frame translation termination codon upstream of the first ATG, this ATG codon is a possible translation initiation codon for this gene.

The ORF of the α2,3-sialyltransferase gene derived from *Photobacterium phosphoreum* strain JT-ISH-467 was composed of 1230 nucleotides and encoded 409 amino acids. This amino acid sequence is shown in SEQ ID NO: 2 in the Sequence Listing. This amino acid sequence contains all of the entire 4 amino acid sequences determined from the purified enzyme. Although the first letter of the N-terminal amino acid sequence has not been decoded, the corresponding amino acid deduced from the gene was Cys (cysteine). Moreover, since the N-terminus of the mature protein corresponds to the 22nd Cys of the sequence shown in SEQ ID NO: 2 in the Sequence Listing, the sequence of the first 21 amino acids was believed to be processed and removed in *Photobacterium phosphoreum*. Genetic information processing software GENETYX Ver.7 (Genetyx Corporation, Japan) was used to analyze full-length homology of the α2,3-sialyltransferase protein and gene derived from *Photobacterium* phosphoreum strain JT-ISH-467 according to the present invention in comparison with their homologues. For the amino acid sequence, there was 32% homology with α2,6-sialyltransferase (JC5898) from *Photobacterium damselae* and 28% homology with a putative protein PM0188 (AAK02272) of *Pasteurella multocida* subsp. *multocida* strain Pm70. For the gene DNA sequence, there was 53% and 51% homology with them, respectively.

(4) Construction of Expression Vector

To test whether the cloned gene had sialyltransferase activity, the full-length of the gene and its derivative modified to remove the N-terminal signal peptide region were each integrated into an expression vector to produce a protein in *E. coli* cells, followed by measuring the activity of this expressed protein.

Genetic information processing software GENETYX Ver.7 was used to analyze the amino acid sequence of α2,3-sialyltransferase derived from *Photobacterium phosphoreum* strain JT-ISH-467, estimating that the N-terminal 24 amino acids would constitute the signal peptide. Then, primers 467-23ST-N0-Pci (SEQ ID NO: 27) and 467-23ST-C0-Bm (SEQ ID NO: 26) for cloning the full-length gene (herein referred to as "467-N0C0 gene"), as well as primers 467-23ST-N2-Nco (SEQ ID NO: 25) and 467-23ST-C0-Bm (SEQ ID NO: 26) for cloning a gene encoding a protein lacking the amino acids of the signal peptide region (herein referred to as "467-N2C0 gene") were designed and synthesized (Table 6).

TABLE 6

| Name | Sequence 5'-3' | Length |
|---|---|---|
| 467-23ST-N2-Nco | GGGCTGTACCATGGACTCTAAGCACAATAACTCAG (SEQ ID NO: 25) | 35mer |
| 467-23ST-C0-Bm | CTTAGAATGGATCCTTACTGCAAATCACTTATCAAC (SEQ ID NO: 26) | 36mer |
| 467-23ST-N0-Pci | AAGGGAATACATGTTCGTTTTTTGTAAAAAAATA (SEQ ID NO: 27) | 34mer |

Restriction enzyme sites PciI (467-23ST-N0-Pci), NcoI (467-23ST-N2-Nco) and BamHI (467-23ST-C0-Bm), which have been integrated into the cloning primers, are underlined. The translation initiation codon ATG and the complementary sequence TAA corresponding to the translation termination codon are boxed. Moreover, within the primer sequences, sequences annealing to the template DNA on the 3' side of the restriction enzyme sites are shown in bold type. The template DNA used for PCR was a plasmid carrying the above 4.6 kb HindIII fragment containing the full-length of the α2,3-sialyltransferase gene derived from *Photobacterium phosphoreum* strain JT-ISH-467. The reaction conditions for PCR were set as follows. In 50 μl reaction solution containing 100 ng template DNA, 5 μl 10×Ex taq buffer, 4 μl 12.5 mM dNTPs, 50 pmol primer and 0.5 μl Ex taq (Takara Bio Inc., Japan), PCR was carried out using a Program Temp Control System PC-700 (ASTEK) under the following conditions: 96° C. for 3 minutes, (96° C. for 1 minute, 50° C. for 1 minute, 72° C. for 2 minutes)×15 cycles, and 72° C. for 6 minutes. As a result, PCR products of approximately 1.2 kb and 1.1 kb were amplified for the 467-N0C0 and 467-N2C0 genes, respectively. In these PCR products, the 467-N0C0 gene was double-digested with restriction enzymes PciI (New England Biolab) and BamHI (Takara Bio Inc., Japan), while the 467-N2C0 gene was double-digested with restriction enzymes NcoI (Takara Bio Inc., Japan) and BamHI, followed by gel purification. pTrc99A (Pharmacia LKB) was used as a vector for *E. coli* expression. After being double-digested with the same restriction enzymes PciI & BamHI or NcoI & BamHI and purified on a gel, this vector was ligated with each restriction enzyme-treated PCR product using a Takara Ligation Kit (Takara Bio Inc., Japan) and transformed into *E. coli* TB1. In a routine manner, the plasmid DNA was extracted and analyzed by restriction enzyme analysis to confirm the integration of the insert. Moreover, the entire nucleotide sequence was determined for the cloned 467-N0C0 and 467-N2C0 genes, thereby confirming that the PCR reaction induced no mutation in their nucleotide sequences. Namely, the cloned 467-N0C0 gene comprised the nucleotide sequence shown in SEQ ID NO: 1, while the cloned 467-N2C0 gene comprised a sequence covering nucleotides 73 to 1230 of SEQ ID NO: 1.

(5) Expression Induction and Activity Measurement

An induction experiment of protein expression was performed on the 467-N0C0 and 467-N2C0 genes obtained in (4) above. A single colony of *E. coli* TB1 having the expression vector pTrc99A carrying either the 467-N0C0 gene or the 467-N2C0 gene was inoculated into LB medium (5 ml) containing an antibiotic, ampicillin (final concentration 100 µl/mL), and pre-cultured at 30° C. to about $A_{600}$=0.5, followed by addition of IPTG (isopropyl-β-D(−)-thiogalactopyranoside, Wako Pure Chemical Industries, Ltd., Japan) at a final concentration of 1 mM. After culturing with shaking at 30° C. for an additional 4 hours, the cells in 2 ml culture solution were collected by centrifugation. These cells were suspended in 200 µl of 20 mM BisTris buffer (pH 7.0) containing 0.336% Triton X-100 and 0.5 M sodium chloride, and ultrasonically homogenized under ice cooling. The resulting homogenate was defined as a crude enzyme solution and provided for activity measurement. The reaction was carried out in duplicate, and the reaction composition was the same as shown in Example 1, except that the reaction time was set to 15 hours. As a result, as shown in Table 7 below, it was demonstrated that there was a factor transferring $^{14}$C-labeled NeuAc in the glycosyl donor CMP-NeuAc to the glycosyl acceptor substrate lactose, i.e., sialyltransferase activity in both crude enzyme solutions from the 467-N0C0 and 467-N2C0 gene transformants. This result indicated that *E. coli* cells introduced with the 467-N0C0 or 467-N2C0 gene expressed sialyltransferase.

TABLE 7

Sialyltransferase activity in *E. coli* homogenate with recombinant β-galactoside-α2,3-sialyltransferase gene derived from JT-ISH-467 strain

| Crude enzyme solution | Radioactivity (cpm) | | |
|---|---|---|---|
| | Round 1 | Round 2 | Average |
| 467-N0C0 | 7097 | 7809 | 7453 |
| 467-N2C0 | 8547 | 8481 | 8514 |
| Absence | 667 | 609 | 638 |

(6) Confirmation of α2,3-sialyltransferase Activity

The crude enzyme solution from (5) above was used to examine whether sialyltransferase expressed by *E. coli* cells introduced with the 467-N2C0 gene had α2,3-sialyltransferase activity. As in the case of Reference Example 1-1, pyridylaminated lactose was used as a glycosyl acceptor to carry out the enzyme reaction. After completion of the reaction, the reaction solution was thermally treated at 95° C. for 5 minutes to deactivate the enzyme, followed by HPLC analysis. It should be noted that the enzyme reaction was accomplished at 25° C. for 6 hours using pyridylaminated lactose and CMP-sialic acid dissolved at 2.0 µM and 5.7 µM, respectively, in 25 µl of 20 mM cacodylate buffer (pH 6.0) (Reaction 1). On the other hand, a control experiment (Reaction 2) was carried out using a reaction solution free from CMP-sialic acid. Further, to clarify the retention time of standards, the crude enzyme solution was deactivated by thermal treatment (95° C., 5 minutes) and tested in the presence of pyridylaminated lactose and pyridylaminated α2,3-sialyllactose.

The analysis results obtained for the standards showed that the retention time was 4.1 minutes for pyridylaminated lactose and 5.4 minutes for pyridylaminated (α-2,3-sialyllactose. This indicated that the peak having a retention time of 5.3 minutes, which was detected in Reaction 1 but not in Reaction 2, corresponded to pyridylaminated α2,3-sialyllactose. Namely, it was proven that sialyltransferase expressed by *E. coli* cells introduced with the 467-N2C0 gene had α2,3-sialyltransferase activity.

The same procedure was repeated to examine whether sialyltransferase expressed by *E. coli* cells introduced with the 467-N0C0 gene had α2,3-sialyltransferase activity. As a result, a peak of pyridylaminated α2,3-sialyllactose was detected as a reaction product in the reaction by *E. coli*-expressed sialyltransferase. Thus, this enzyme was found to have α2,3-sialyltransferase activity.

Reference Example 1-5

Cloning and Nucleotide Sequence Analysis of α2,3-sialyltransferase Gene Derived from *Photobacterium* sp. Strain JT-ISH-224, and *E. coli* Expression of the Gene (1) Confirmation of β-galactoside-α2,3-sialyltransferase Activity in JT-ISH-224 Strain and the Presence of its Enzyme Gene To determine whether there was a homologue of the α2,3-sialyltransferase gene derived from *Photobacterium phosphoreum* strain JT-ISH-467, genomic Southern hybridization was performed on *Photobacterium* sp. strain JT-ISH-224 that was found to have sialyltransferase activity in Reference Example 1-1. After genomic DNA was prepared from a cell pellet of the JT-ISH-224 strain, as described in Reference Example 1-4, the genomic DNA of the JT-ISH-224 strain was digested with a restriction enzyme EcoRI or HindIII and fractionated by 0.7% agarose gel electrophoresis, followed by alkaline blotting with 0.4 M NaOH to transfer the gel onto a Hybond-N+ nylon membrane filter (Amersham Biosciences). Southern hybridization was performed on this filter, as described in Reference Example 1-4, using as a probe the above partial fragment (929 bp; SEQ ID NO: 17) of the α2,3-sialyltransferase gene derived from the JT-ISH-467 strain, except that the hybridization and washing temperatures were set to 55° C. As a result, EcoRI digestion detected a band of 16 kb, while HindIII digestion detected bands of 5 kb and 2.7 kb. These results indicated that the JT-ISH-224 strain had a homologue of the α2,3-sialyltransferase gene derived from the JT-ISH-467 strain.

(2) Cloning of α2,3-sialyltransferase Gene Derived from JT-ISH-224 Strain

Next, the α2,3-sialyltransferase gene of the JT-ISH-224 strain was cloned. λDASH II (Stratagene) was used to construct a genomic library from the genomic DNA of the JT-ISH-224 strain, as described in Reference Example 1-4. The partial fragment (929 bp; SEQ ID NO: 17) of the α2,3-sialyltransferase gene derived from the JT-ISH-467 strain was used as a probe to screen the genomic library of the JT-ISH-224 strain, except that the hybridization and washing temperatures were set to 55° C., as in the case of Reference Example 1-4. As a result, 12 clones were obtained up to the end of secondary screening (also serving as plaque purification), 6 of which were treated with a QIAGEN Lambda Mini Kit (QIAGEN) to purify their λDNAs, as described in Reference Example 1-4. Further, 3 of these λDNA samples and the total genomic DNA of the JT-ISH-224 strain were digested with a restriction enzyme EcoRI or HindIII. Each digest was fractionated by agarose gel electrophoresis and transferred onto a nylon membrane filter, as described above. This filter was provided for Southern analysis using as a probe the partial fragment (929 bp; SEQ ID. NO: 17) of the α2,3-sialyltransferase gene derived from the JT-ISH-467 strain. The hybridization and washing temperatures were set to 55° C. As a result, EcoRI digestion detected a band of 12 kb or larger, while HindIII digestion detected two bands of 5 kb and 2.7 kb for each of the 3 λDNA samples and the total genomic DNA of the JT-ISH-224 strain. Then, each λDNA sample was digested again with HindIII, followed by gel purification to purify these two DNA fragments of 5 kb and 2.7 kb, each of which was then cloned in a routine manner into a HindIII site of plasmid vector pBluescript SK(−).

Next, nucleotide sequences at both ends of the 5 kb HindIII fragment and the 2.7 kb HindIII fragment were determined for these clones using M13 primers (Takara Bio Inc., Japan) in an ABI PRISM fluorescent sequencer (Model 310 Genetic Analyzer, Perkin Elmer). As a result, amino acid sequences deduced from the DNA sequence on one side of the kb fragment and the DNA sequence on one side of the 2.7 kb fragment showed homology with sialyltransferase when analyzed by database search. To completely determine DNA of the gene for the enzyme of the JT-ISH-224 strain, the primer shown in Table 8 below was synthesized on the basis of the DNA sequence obtained from the 2.7 kb HindIII fragment, and used for nucleotide sequencing.

TABLE 8

| Name | Sequence 5'-3' | Length |
| --- | --- | --- |
| 224-23ST-inRV1 | CAGGAACTGCAACAGCAGAG (SEQ ID NO: 34) | 20mer |

As a result, the sequence of SEQ ID NO: 28 in the Sequence Listing was obtained. This sequence corresponds to the entire nucleotide sequence of the open reading frame (ORF) of the α2,3-sialyltransferase gene derived from the JT-ISH-224 strain. Since there is an in-frame translation termination codon upstream of the first ATG, this ATG codon is a possible translation initiation codon for this gene. The ORF of the α2,3-sialyltransferase gene derived from *Photobacterium* sp. strain JT-ISH-224 was composed of 1230 nucleotides and encoded 409 amino acids, as in the case of the α2,3-sialyltransferase gene derived from *Photobacterium phosphoreum* strain JT-ISH-467. This amino acid sequence is shown in SEQ ID NO: 29 in the Sequence Listing. The gene had an internal HindIII site. GENETYX Ver.7 was used to analyze nucleic acid and amino acid sequences, indicating that the α2,3-sialyltransferase gene derived from the JT-ISH-224 strain had 92% homology with the α2,3-sialyltransferase gene derived from the JT-ISH-467 strain. For the amino acid sequence, there was 92% homology with α2,3-sialyltransferase derived from the JT-ISH-467 strain. Moreover, the amino acid sequence of α2,3-sialyltransferase derived from the JT-ISH-224 strain had 33% homology with α2,6-sialyltransferase (JC5898) from *Photobacterium damselae* and 29% homology with a putative protein PM0188 (AAK02272) of *Pasteurella multocida* subsp. *multocida* strain Pm70. For the gene DNA sequence, there was 54% and 50% homology with them, respectively.

(3) Construction of Expression Vector

To test whether the cloned gene had sialyltransferase activity, the full-length of the gene and its derivative modified to remove the N-terminal signal peptide region were each integrated into an expression vector to produce a protein in *E. coli* cells, followed by measuring the activity of this expressed protein.

Genetic information processing software GENETYX Ver.7 was used to analyze the amino acid sequence of α2,3-sialyltransferase derived from the JT-ISH-224 strain, estimating that the N-terminal 24 amino acids would constitute the signal peptide. Then, primers 224-23ST-N0-Pci (SEQ ID NO: 35) and 224-23ST-C0new-Bm (SEQ ID NO: 37) for cloning the full-length gene (herein referred to as "224-N0C0 gene"), as well as primers 224-23ST-N1-Nco (SEQ ID NO: 36) and 224-23ST-C0new-Bm (SEQ ID NO: 37) for cloning a gene encoding a protein lacking the amino acids of the signal peptide region (herein referred to as "224-N1C0 gene") were designed and synthesized (Table 9).

TABLE 9

| Name | Sequence 5'-3' | Length |
| --- | --- | --- |
| 224-23ST-N0-Pci | AAGGGAATACATGTTCGTTTTTTGTAAAAAAATG (SEQ ID NO: 35) | 34mer |
| 224-23ST-N1-Nco | GGGATGTACCATGGACTCTAATCACAATAACTCAG (SEQ ID NO: 36) | 35mer |
| 224-23ST-C0new-Bm | ATTAAAATGGATCCTTACTGCAAATCACTTATCAAC (SEQ ID NO: 37) | 36mer |

Restriction enzyme sites PciI (224-23ST-N0-Pci), NcoI (224-23ST-N-1-Nco) and BamHI (224-23ST-C0new-Bm), which have been integrated into the cloning primers, are underlined. The translation initiation codon ATG and the complementary sequence TAA corresponding to the translation termination codon are boxed. Moreover, within the primer sequences, sequences annealing to the template DNA are shown in bold type. In the case of primer 224-23ST-N0-Pci, cytosine (C) located immediately after the translation initiation codon ATG is replaced by thymine (T) as a result of introducing the PciI site for the subsequent cloning. For this reason, the amino acid sequence located immediately after the translation initiation methionine is changed from leucine (Leu) to phenylalanine (Phe). This mutation was judged to be less likely to cause a great change in enzyme activity because both Leu and Phe are members of hydrophobic amino acids and because this site is within the signal peptide region.

Subsequently, PCR was carried out to amplify the α2,3-sialyltransferase gene derived from the JT-ISH-224 strain for use in integration into an expression vector. The template DNA used was the above λDNA containing the α2,3-sialyltransferase gene derived from the JT-ISH-224 strain. The reaction conditions for PCR were set as follows. In 50 μl reaction solution containing 100 ng template DNA, 5 μl 10×Ex taq buffer, 4 μl 2.5 mM dNTPs, 50 pmol primer and 0.5 μl Ex taq (Takara Bio Inc., Japan), PCR was carried out using a Program Temp Control System PC-700 (ASTEK) under the following conditions: 96° C. for 3 minutes, (96° C. for 1 minute, 50° C. for 1 minute, 72° C. for 2 minutes)×15 cycles, and 72° C. for 6 minutes. As a result, PCR products of approximately 1.2 kb and 1.1 kb were amplified for the 224-N0C0 and 224-N1C0 genes, respectively. These PCR products were double-digested with restriction enzymes PciI (New England Biolab) and BamHI (for the 224-N0C0 gene)

or with restriction enzymes NcoI and BamHI (for the 224-N1C0 gene), followed by gel purification. pTrc99A was used as a vector for E. Coli expression. After being double-digested with the same restriction enzymes PciI & BamHI (for introduction of the 224-N0C0 gene) or NcoI & BamHI (for introduction of the 224-N1C0 gene) and purified on a gel, this vector was ligated with each restriction enzyme-treated PCR product using a Takara Ligation Kit (Takara Bio Inc., Japan) and transformed into E. coli TB1. In a routine manner, the plasmid DNA was extracted and analyzed by restriction enzyme analysis to confirm the integration of the insert. Further, the entire nucleotide sequence was confirmed for the cloned 224-N0C0 and 224-N1C0 genes. As a result, the 224-N0C0 gene was confirmed to have the above replacement of cytosine (C) by thymine (T), but there was no other mutation in its nucleotide sequence. Likewise, the 224-N1C0 gene had no mutation in its nucleotide sequence and comprised a desired nucleotide sequence, i.e., nucleotides 73 to 1230 of SEQ ID NO: 28 in the Sequence Listing.

(4) Expression Induction and Activity Measurement

In the same manner as shown in Reference Example 1-4, an induction experiment of protein expression was performed on 2 clones, i.e., the 224-N0C0 and 224-N1C0 genes to measure their enzymatic activity. As a result, as shown in Table 10 below, sialyltransferase activity was observed in both crude enzyme solutions from the 224-N0C0 and 224-N1C0 gene transformants.

TABLE 10

Sialyltransferase activity in E. coli homogenate with JT-ISH-224-derived recombinant homologue of β-galactoside-α2,3-sialyltransferase gene derived from JT-ISH-467 strain

| Crude enzyme solution | Radioactivity (cpm) | | |
|---|---|---|---|
| | Round 1 | Round 2 | Average |
| 224-N0C0 | 9273 | 8468 | 8870.5 |
| 224-N1C0 | 9330 | 9415 | 9672.5 |
| Absence | 667 | 609 | 638 |

(5) Confirmation of α2,3-sialyltransferase Activity

In the same manner as shown in Reference Example 1-4, the 224-N0C0 and 224-N1C0 genes were each introduced into E. coli cells to express the encoded enzyme, followed by reaction using pyridylaminated lactose as a glycosyl acceptor to examine the enzyme for its α2,3-sialyltransferase activity. As a result of HPLC evaluation on the reaction product of each sialyltransferase expressed by E. coli cells, a peak of pyridylaminated α2,3-sialyllactose was detected for each clone. This result indicated that sialyltransferase derived from the JT-ISH-224 strain had α2,3-sialyltransferase activity.

Reference Example 1-6

Cloning and Nucleotide Sequence Analysis of α2,3-sialyltransferase Gene Derived from Vibrio sp. Strain JT-FAJ-16, and E. coli Expression of the Gene (1) Confirmation of β-galactoside-α2,3-sialyltransferase Activity in JT-FAJ-16 Strain and the Presence of its Enzyme Gene To determine whether there was a homologue of the α2,3-sialyltransferase gene derived from Photobacterium phosphoreum strain JT-ISH-467, genomic Southern hybridization was performed on Vibrio sp. strain JT-FAJ-16 that was found to have sialyltransferase activity in Reference Example 1-1. After genomic DNA was prepared from a cell pellet of the JT-FAJ-16 strain, as described in Reference Example 1-4, the genomic DNA was digested with restriction enzymes EcoRI and HindIII and fractionated by 0.7% agarose gel electrophoresis, followed by alkaline blotting with 0.4 M NaOH to transfer the gel onto a Hybond-N+ nylon membrane filter (Amersham Biosciences). Southern hybridization was performed on this filter, as described in Reference Example 1-4, using the above 929 bp probe (SEQ ID NO: 17), except that the hybridization and washing temperatures were set to 55° C. As a result, EcoRI digestion detected a band of 3.6 kb, while HindIII digestion detected a band of 7 kb. This indicated that the JT-FAJ-16 strain had a homologue of the α2,3-sialyltransferase gene derived from the JT-ISH-467 strain.

(2) Cloning of α2,3-sialyltransferase Gene Derived from JT-FAJ-16 Strain

Next, the α2,3-sialyltransferase gene of the JT-FAJ-16 strain was cloned. λDASH II (Stratagene) was used to construct a genomic library from the genomic DNA of the JT-FAJ-16 strain, as described in Reference Example 1-4. The partial fragment (929 bp; SEQ ID NO: 17) of the α2,3-sialyltransferase gene derived from the JT-ISH-467 strain was used as a probe to screen the genomic library of the JT-FAJ-16 strain, except that the hybridization experiment was performed using an ECL direct labelling & detection system (Amersham Biosciences). The probe was prepared according to the instructions attached to the kit. Hybridization was accomplished at 37° C. for 4 hours using the hybridization buffer included in the kit, which was supplemented with 5% (w/v) blocking reagent and 0.5 M NaCl. Washing was performed twice in 0.4% SDS, 0.5×SSC at 50° C. for 20 minutes and once in 2×SSC at room temperature for 5 minutes. Signal detection was performed according to the instructions attached to the kit.

As a result, the primary screening (also serving as plaque purification) resulted in 12 clones, 6 of which were treated with a QIAGEN Lambda Mini Kit (QIAGEN) to purify their λDNAs, as described in Reference Example 1-4. Further, these λDNA samples and the total genomic DNA of the JT-FAJ-16 strain were digested with a restriction enzyme EcoRI. Each digest was fractionated by agarose gel electrophoresis and transferred onto a nylon membrane filter, as described above. This filter was provided for Southern analysis with an ECL system under the same conditions as shown above using as a probe the partial fragment (929 bp; SEQ ID NO: 17) of the α2,3-sialyltransferase gene derived from the JT-ISH-467 strain. As a result, a band of 3.6 kb was detected for each of the 6 λDNA samples and the total genomic DNA of the JT-FAJ-16 strain. Then, each λDNA sample was digested again with EcoRI, followed by gel purification to purify this 3.6 kb DNA fragment, which was then cloned in a routine manner into an EcoRI site of plasmid vector pBluescript SK(−).

Next, nucleotide sequences at both ends were determined for the 3.6 kb EcoRI fragment that appeared to contain the α2,3-sialyltransferase gene derived from the JT-FAJ-16 strain, using M13 primers (Takara Bio Inc., Japan) in an ABI PRISM fluorescent sequencer (Model 310 Genetic Analyzer, Perkin Elmer). As a result, an amino acid sequence deduced from the DNA sequence at one end showed 27% homology with α2,6-sialyltransferase (JC5898) from Photobacterium damselae when analyzed by database search. To completely determine the entire nucleotide sequence of the α2,3-sialyltransferase gene of the JT-FAJ-16 strain, the primers shown in Table 11 below were synthesized on the basis of the DNA sequence obtained from the 3.6 kb EcoRI fragment, and used for nucleotide sequencing.

TABLE 11

| Name | Sequence 5'-3' | Length |
| --- | --- | --- |
| FAJEc3.6RV1 | TTC AAA ACT GCC TGA GTC AG (SEQ ID NO: 38) | 20mer |
| FAJEc3.6RV2 | ATT TCA TGG TCT AGA TAC CC (SEQ ID NO: 39) | 20mer |

Based on the resulting nucleotide sequence data, the primers shown in Table 12 below were further designed and synthesized to determine the entire nucleotide sequence.

TABLE 12

| Name | Sequence 5'-3' | Length |
| --- | --- | --- |
| FAJ23STinFW3 | CTG ACT CAG GCA GTT TTG AA (SEQ ID NO: 40) | 20mer |
| FAJ23STinFW4 | GAA AGC AAC TCT CTC AAT GGG (SEQ ID NO: 41) | 21mer |
| FAJ23STinRV3 | ATA AAC CCA TTG AGA GAG TTG (SEQ ID NO: 42) | 21mer |

As a result, the sequence of SEQ ID NO: 30 in the Sequence Listing was obtained. This sequence corresponds to the entire nucleotide sequence of the open reading frame (ORF) of the α2,3-sialyltransferase gene derived from the JT-FAJ-16 strain. Since there is an in-frame translation termination codon upstream of the first ATG, this ATG codon is a possible translation initiation codon for this gene. The ORF of the α2,3-sialyltransferase gene derived from the JT-FAJ-16 strain was composed of 1209 nucleotides and encoded 402 amino acids. This amino acid sequence is shown in SEQ ID NO: 31 in the Sequence Listing. GENETYX Ver.7 was used to analyze nucleic acid and amino acid sequences, indicating that the α2,3-sialyltransferase gene derived from the JT-FAJ-16 strain had 69.7% and 68% homology with the α2,3-sialyltransferase genes derived from the JT-ISH-467 and JT-ISH-224 strains, respectively. For the amino acid sequence, there was 64.7% and 64.8% homology with them, respectively. Moreover, the amino acid sequence of α2,3-sialyltransferase derived from the JT-FAJ-16 strain had 30.5% homology with α2,6-sialyltransferase (JC5898) from *Photobacterium damselae* and 27.3% homology with a putative protein PM0188 (AAK02272) of *Pasteurella multocida* subsp. *multocida* strain Pm70. For the gene DNA sequence, there was 51.2% and 48.3% homology with them, respectively.

(3) Construction of Expression Vector

To test whether the cloned gene had sialyltransferase activity, the full-length of the gene and its derivative modified to remove the N-terminal signal peptide region were each integrated into an expression vector to produce a protein in *E. coli* cells, followed by measuring the activity of this expressed protein.

Genetic information processing software GENETYX Ver.7 was used to analyze the amino acid sequence of α2,3-sialyltransferase derived from the JT-FAJ-16 strain, estimating that the N-terminal 22 amino acids would constitute the signal peptide. Then, primers FAJ23STN0-BspHI (SEQ ID NO: 43) and FAJ23STC0-BamHI (SEQ ID NO: 45) for cloning the full-length gene (herein referred to as "FAJ-N0C0 gene"), as well as primers FAJ23STN1-BspHI (SEQ ID NO: 44) and FAJ23STC0-BamHI (SEQ ID NO: 45) for cloning a gene encoding a protein lacking the amino acids of the signal peptide region (herein referred to as "FAJ-N1C0 gene") were designed and synthesized (Table 13).

TABLE 13

| Name | Sequence 5'-3' | Length |
| --- | --- | --- |
| FAJ23STN0-BspHI | TGGATAACTCATGAAAAACATTATAACAAAAAGAATG (SEQ ID NO: 43) | 37mer |
| FAJ23STN1-BspHI | TATTATCGTCATGAACAATGATAACAGCACTACC (SEQ ID NO: 44) | 34mer |
| FAJ23STC0-BamHI | TCTTTTTAGGATCCTTAAATGTCGCTGATTAGTTTTAT (SEQ ID NO: 45) | 38mer |

Restriction enzyme sites BspHI (FAJ23STN0-BspHI, FAJ23STN1-BspHI) and BamHI (FAJ23STC0-BamHI), which have been integrated into the cloning primers, are underlined. The translation initiation codon ATG and the complementary sequence TAA corresponding to the translation termination codon are boxed. Moreover, within the primer sequences, sequences annealing to the template DNA are shown in bold type. PCR was carried out using these primers to amplify the α2,3-sialyltransferase gene derived from the JT-FAJ-16 strain for use in integration into an expression vector. The template DNA used was the above 3.6 kb DNA fragment containing the gene. The reaction conditions for PCR were set as follows. In 50 μl reaction solution containing 300 ng template DNA, 5 μl 10×Ex taq buffer, 4 μl 2.5 mM dNTPs, 50 pmol primer and 0.5 μl Ex taq (Takara Bio Inc., Japan), PCR was carried out using a Program Temp Control System PC-700 (ASTEK) under the following conditions: 96° C. for 3 minutes, (96° C. for 1 minute, 50° C. for 1 minute, 72° C. for 2 minutes)×10 cycles, and 72° C. for 6 minutes. As a result, PCR products of approximately 1.2 kb and 1.1 kb were amplified for FAJ-N0C0 and FAJ-N1C0, respectively. These PCR products were each cloned into a TA cloning vector pCR2.1TOPO (Invitrogen) according to the instructions attached to a TA cloning kit (Invitrogen). The *E.* coli used was TB1. The plasmid was purified from the resulting colonies in a routine manner, and the introduction of each PCR product into the vector was confirmed with a restriction enzyme EcoRI. The plasmid samples confirmed for the introduction were double-digested with restriction enzymes BspHI and BamHI, followed by gel purification to purify a fragment of 1.2 kb (FAJ-N0C0 gene) or 1.1 kb (FAJ-N1C0 gene). Using a Takara Ligation Kit (Takara Bio Inc., Japan), these DNA samples were each ligated to a vector for *E. coli* expression, pTrc99A, which had been double-digested with restriction enzymes NcoI and BamHI. Each vector was integrated into *E. coli* TB1 cells. In a routine manner, the plasmid DNA was extracted and analyzed by restriction enzyme analysis to confirm the integration of the insert. Further, the entire nucleotide sequence was confirmed for the cloned FAJ-N0C0 and FAJ-N1C0 genes. The FAJ-N0C0 gene had no mutation in its nucleotide sequence and comprised a desired nucleotide sequence, i.e., nucleotides 1 to 1209 of SEQ ID NO: 30 in the Sequence Listing. Likewise, the FAJ-N1C0 gene had no mutation in its nucleotide sequence and comprised a desired nucleotide sequence, i.e., nucleotides 67 to 1209 of SEQ ID NO: 30 in the Sequence Listing.

(4) Expression Induction and Activity Measurement

In the same manner as shown in Reference Example 1-4, an induction experiment of protein expression was performed on 2 clones, i.e., the FAJ-N0C0 and FAJ-N0C0 genes to measure their enzyme activity. As a result, as shown in Table 14 below, sialyltransferase activity was observed in both crude enzyme solutions from the FAJ-N0C0 and FAJ-N1C0 gene transformants.

TABLE 14

Sialyltransferase activity in *E. coli* homogenate with JT-FAJ-16-derived recombinant homologue of β-galactoside-α2,3-sialyltransferase gene derived from JT-ISH-467 strain

| Crude enzyme solution | Radioactivity (cpm) | | |
|---|---|---|---|
| | Round 1 | Round 2 | Average |
| FAJ-N0C0 | 11012 | 12056 | 11534 |
| FAJ-N1C0 | 5664 | 6724 | 6194 |
| Absence | 232 | 110 | 171 |

(5) Confirmation of α2,3-sialyltransferase Activity

In the same manner as shown in Reference Example 1-4, the FAJ-N0C0 and FAJ-N1C0 genes were each introduced into *E. coli* cells to express the encoded enzyme, followed by reaction using pyridylaminated lactose as a glycosyl acceptor to examine the enzyme for its α2,3-sialyltransferase activity. As a result of HPLC analysis on the reaction product of each sialyltransferase expressed by *E. coli* cells, a peak of pyridylaminated α2,3-sialyllactose was detected for each clone. This result indicated that sialyltransferase derived from the JT-FAJ-16 strain had α2,3-sialyltransferase activity.

Example 1

Effect of NaCl on Enzymatic Activity of glycosyltransferase (α2,6-sialyltransferase) Derived From *P. damselae* strain JT0160

Material and Method

β-Galactoside-α2,6-sialyltransferase was purified from *P. damselae* strain JT0160, a marine microorganism, according to the procedure previously reported (Japanese Patent No. 3062409). The purity of the purified enzyme was confirmed by SDS-PAGE, whereby the final purified enzyme was confirmed to be an electrophoretically single protein. This purified enzyme was used in the following experiment.

The enzymatic reaction was accomplished in 20 μl reaction solution containing CMP-$^{14}$C-NeuAc as a glycosyl donor substrate (50.066 nmol, 25000 cpm), lactose as a glycosyl acceptor substrate (1 mmol), sialyltransferase (0.5 to 1.5 mU) and NaCl at a concentration varying from 0 to 2.5 M (30° C., 1 minute). After completion of the enzyme reaction, the radioactivity of NeuAc which was transferred to lactose under the respective conditions was measured to calculate the enzymatic activity, thereby studying the effect of NaCl on the enzymatic activity in each test range.

More specifically, after completion of the reaction, each reaction solution was supplemented with 1.98 ml of 5 mM phosphate buffer (pH 6.8) and applied to a AG1–×2Resin ($PO_4^{3-}$ form, 0.2×2 cm) column. This column was prepared as follows: AG1–×2Resin (OH$^-$ form) (BIO-RAD) was suspended in 1 M phosphate buffer (pH 6.8), and after 30 minutes, the resin was washed with distilled water and then suspended in distilled water. The eluate (0 to 2 ml) from this column was measured for its radioactivity. The eluate from this column contains unreacted lactose and $^{14}$C-NeuAc (N-acetylneuraminic acid)-bound sialyllactose which was generated by the reaction, but unreacted CMP-$^{14}$C-NeuAc is still retained on the column. Thus, the radioactivity of $^{14}$C from sialyllactose generated as a result of the enzymatic reaction arises exclusively from the reaction product, so that the radioactivity of this fraction can be used to calculate the enzymatic activity.

Results

Sialyltransferase derived from *P. damselae* strain JT0160 was found to enhance its enzymatic activity due to the presence of NaCl in the enzymatic reaction system. In the presence of NaCl at a concentration of 0.2 M to 1 M in the enzymatic reaction system, the enzyme activity was improved about 1.2- to 1.4-fold when compared to the absence of NaCl (FIG. 1).

Example 2

Effect of KCl on Enzymatic Activity of glycosyltransferase (α2,6-sialyltransferase) Derived From *P. damselae* strain JT0160

Material and Method

In the same manner as shown in Example 1, β-galactoside-α2,6-sialyltransferase was completely purified from *P. damselae* strain JT0160 and used in the following experiment.

The enzyme reaction was accomplished in 20 μl reaction solution containing CMP-$^{14}$C-NeuAc as a glycosyl donor substrate (50.066 nmol, 25000 cpm), lactose as a glycosyl acceptor substrate (1 mmol), sialyltransferase (0.5 to 1.5 mU) and KCl at a concentration varying from 0 to 1 M (30° C., 1 minute). After completion of the enzyme reaction, the radioactivity of NeuAc which was transferred to lactose under the respective conditions was measured to calculate the enzyme activity, thereby studying the effect of KCl on the enzyme activity in each test range. More specifically, after completion of the reaction, each reaction solution was supplemented with 1.98 ml of 5 mM phosphate buffer (pH 6.8) and applied to a AG1–×2Resin ($PO_4^{3-}$ form, 0.2×2 cm) column. This column was prepared as follows: AG1–×2Resin (OH$^-$ form) (BIO-RAD) was suspended in 1 M phosphate buffer (pH 6.8), and after 30 minutes, the resin was washed with distilled water and then suspended in distilled water. The eluate (0 to 2 ml) from this column was measured for its radioactivity.

Results

Figure 2:
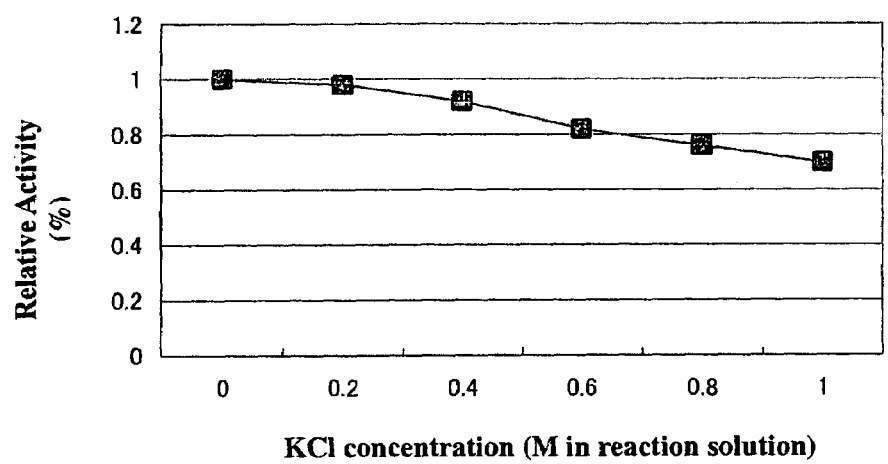
FIG. 2 is a graph showing the effect of KCl on the enzyme activity of glycosyltransferase (α2,6-sialyltransferase; native) derived from a bacterium belonging to the genus Photobacterium (Photobacterium damselae).

KCl added at various concentrations to the enzymatic reaction system was not observed to improve the activity of sialyltransferase derived from *P. damselae* strain JT0160 (FIG. 2).

Example 3

Effect of Divalent Ion-containing Salts on Enzyme Activity of glycosyltransferase Derived From *P. damselae* strain JT0160

Material and Method

In the same manner as shown in Example 1, β-galactoside-α2,6-sialyltransferase was purified from *P. damselae* strain JT0160 and used in the following experiment.

The enzyme reaction was accomplished in 20 μl reaction solution containing CMP-$^{14}$C-NeuAc as a glycosyl donor substrate (50.066 nmol, 25000 cpm), lactose as a glycosyl acceptor substrate (1 mmol), sialyltransferase (0.5 to 1.5 mU) and any one of $MgCl_2$, $MgSO_4$, $CoCl_2$, $CaCl_2$, $MnCl_2$ or $FeSO_4$ at a final concentration of 0 mM, 10 mM or 20 mM. (30° C., 1 minute). After completion of the enzyme reaction, the radioactivity of NeuAc which was transferred to lactose under the respective conditions was measured to calculate the enzyme activity, thereby studying the effect of various salts on the enzyme activity in each test range. More specifically, after completion of the reaction, each reaction solution was supplemented with 1.98 ml of 5 mM phosphate buffer (pH 6.8) and applied to a AG1-×2Resin ($PO_4^{3-}$ form, 0.2×2 cm) column. This column was prepared as follows: AG1-×2Resin (OH$^-$ form) (BIO-RAD) was suspended in 1 M phosphate buffer (pH 6.8), and after 30 minutes, the resin was washed with distilled water and then suspended in distilled water. The eluate (0 to 2 ml) from this column was measured for its radioactivity.

Results

None of the various divalent ion-containing salts in the reaction solution was observed to improve the activity of α2,6-sialyltransferase derived from *P. damselae* strain JT0160 (Table 15).

TABLE 15

Relationship of relative activity with type and concentration of various inorganic salts added to reaction solution

|  | 10 mM | 20 mM |
| --- | --- | --- |
| Absence | 1 | 1 |
| $MgCl_2$ | 0.97 | 0.84 |
| $MgSO_4$ | 0.87 | 0.89 |
| $MnCl_2$ | 0.78 | 0.92 |
| $CaCl_2$ | 0.86 | 0.82 |
| $CoCl_2$ | 0.69 | 0.41 |
| $FeSO_4$ | 0.85 | 0.93 |

Example 4

Effect of NaCl on Enzyme Activity of Rat Liver-Derived Sialyltransferase (α2,6-sialyltransferase)

Material and Method

Rat liver-derived β-galactoside-α2,6-sialyltransferase (Wako Pure Chemical Industries, Ltd., Japan) was used in the following experiment according to the procedures for enzymatic activity measurement attached to the enzyme, with minor modifications.

The enzyme reaction was accomplished in the presence of CMP-$^{14}$C-NeuAc as a glycosyl donor substrate (50.066 nmol, 25000 cpm), asialofetuin as a glycosyl acceptor substrate (10 mg), sialyltransferase (1 to 5 mU) and NaCl at a concentration varying from 0 to 1.4 M (37° C., 1 hour). After completion of the enzymatic reaction, each reaction solution was applied to a Sephadex G-50 super fine (Amersham) column (0.8×20 cm) and eluted using a 0.1 M NaCl solution as a mobile phase to collect a high-molecular fraction containing a reaction product eluted at 2 to 4 ml (i.e., an enzymatic reaction product in which $^{14}$C-labeled NeuAc was transferred to asialofetuin). It should be noted that a control experiment was performed for each reaction to confirm that unreacted CMP-$^{14}$C-NeuAc was not eluted in this fraction. The radioactivity of NeuAc transferred to asialofetuin was measured from the fraction to calculate the enzyme activity.

Results

Figure 3:
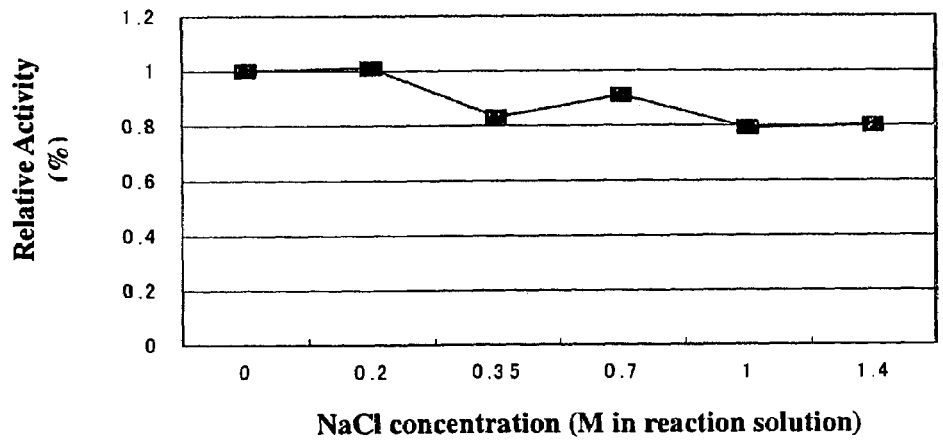
FIG. 3 is a graph showing the effect of NaCl on the enzyme activity of rat-derived glycosyltransferase (α2,6-sialyltransferase).

The results obtained are shown in FIG. 3, expressed as relative activity compared to that of NaCl-free reaction solution, which was set to 1. In rat liver-derived β-galactoside-α2,6-sialyltransferase, addition of NaCl caused no increase in its enzyme activity.

Example 5

Effect of NaCl on Enzyme Activity of glycosyltransferase (crude α2,6-sialyltransferase) Prepared From Various Strains Belonging to *Photobacterium damselae*

Material and Method

ATCC33539T and ATCC35083, which were strains belonging to *Photobacterium damselae* but different from JT0160, were cultured and the resulting cells were used to prepare crude enzyme solutions according to the procedure for preparing a crude enzyme solution of *P. damselae* JT0160 (Purification and characterization of a Marine bacterial β-Galactoside α2,6-Sialyltransferase from *Photobacterium damselae* JT0160 J. Biochem. 120, 104-110, 1996). These crude enzymes were used in the following experiment.

The enzyme reaction was accomplished in 20 μl reaction solution containing CMP-$^{14}$C-NeuAc as a glycosyl donor substrate (50.066 nmol, 25000 cpm), lactose as a glycosyl acceptor substrate (1 mmol), glycosyltransferase derived from various strains (1 mU or less) and NaCl at a concentration of 0.5 M (30° C., 1 minute). After completion of the enzymatic reaction, the radioactivity of NeuAc which was transferred to lactose under the respective conditions was measured to calculate the enzyme activity, thereby studying the effect of NaCl on the enzyme activity in each test range. More specifically, after completion of the reaction, each reaction solution was supplemented with 1.98 ml of 5 mM phosphate buffer (pH 6.8) and applied to a AG1-×2Resin ($PO_4^{3-}$ form, 0.2×2 cm) column. This column was prepared as follows: AG1-×2Resin (OH$^-$ form) (BIO-RAD) was suspended in 1 M phosphate buffer (pH 6.8), and after 30 minutes, the resin was washed with distilled water and then suspended in distilled water. The eluate (0 to 2 ml) from this column was measured for its radioactivity.

Results

In the presence of 0.5 M NaCl in the reaction system, the enzyme activity of glycosyltransferase was improved in each strain. Although the degree of improvement varied from strain to strain, the enzymatic activity was improved by about 1.2- to to 1.3-fold (Table 16).

TABLE 16

Effect of NaCl on activity of glycosyltransferase derived from microorganisms belonging to the genus *Photobacterium*

| Strain name | | Radioactivity | +NaCl/−NaCl |
|---|---|---|---|
| Negative control | −Lac | 86.5 | |
| | −NaCl | 117 | |
| | +NaCl | 302 | |
| *P. damsela* ATCC33539 | −Lac | 741 | 1.2 |
| | −NaCl | 8763 | |
| | +NaCl | 11071 | |
| *P. damsela* ATCC35083 | −Lac | 445 | 1.3 |
| | −NaCl | 7243 | |
| | +NaCl | 9733 | |

Example 6

Effect of NaCl on Enzyme Activity of glycosyltransferase (Deletion Mutant of Recombinant α2,6-sialyltransferase; N2C1) Derived From *P. damselae* JT0160

Material and Method

A deletion mutant (N2C1) of the β-galactoside-α2,6-sialyltransferase gene derived from *P. damselae* strain JT0160 was prepared and recombinated into an expression plasmid, which was then used to transform *E. coli* cells. The transformed *E. coli* cells were cultured at 30° C. at 180 rpm for 12 hours in L Broth (containing ampicillin at a final concentration of 0.2 mg/ml and IPTG at a final concentration of 1 mM), followed by centrifugation to collect the cells. The collected cells were suspended in 20 mM sodium cacodyrate buffer (pH 5.0) and then ultrasonicated at 4° C. to homogenize the cells, thereby preparing a crude enzyme solution containing a sialyltransferase protein from the N2C1 gene. When compared to the amino acid sequence deduced from the gene sequence encoding β-galactoside-α2,6-sialyltransferase derived from *P. damselae* strain JT0160, the N2C1 gene-derived sialyltransferase protein lacks the N-terminal (Met) 107 amino acid residues and the C-terminal 176 amino acid residues of the above amino acid sequence, but has substantially the same enzymatic activity as the native enzyme. This N2C1 gene-derived sialyltransferase protein was used in the following experiment.

The enzyme reaction was accomplished in 20 µl reaction solution containing CMP-$^{14}$C-NeuAc as a glycosyl donor substrate (50.066 nmol, 25000 cpm), lactose as a glycosyl acceptor substrate (1 mmol), N2C1 (0.5 to 1.5 mU) and NaCl at a concentration varying from 0 to 2.5 M (30° C., 1 minute). After completion of the enzyme reaction, the radioactivity of NeuAc which was transferred to lactose under the respective conditions was measured to calculate the enzyme activity, thereby studying the effect of NaCl on the enzyme activity in each test range.

More specifically, after completion of the reaction, each reaction solution was supplemented with 1.98 ml of 5 mM phosphate buffer (pH 6.8) and applied to a AG1−x2Resin ($PO_4^{3-}$ form, 0.2×2 cm) column. This column was prepared as follows: AG1−x2Resin (OH⁻ form) (BIO-RAD) was suspended in 1 M phosphate buffer (pH 6.8), and after 30 minutes, the resin was washed with distilled water and then suspended in distilled water. The eluate (0 to 2 ml) from this column was measured for its radioactivity.

Results

Figure 4:
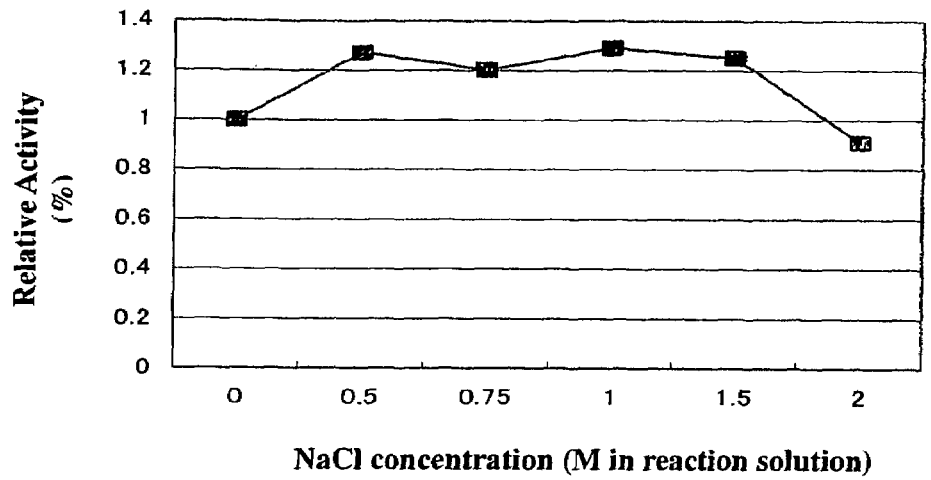
FIG. 4 is a graph showing the effect of NaCl on the enzyme activity of glycosyltransferase (a deletion mutant of recombinant α2,6-sialyltransferase; N2C1) derived from a bacterium belonging to the genus Photobacterium (Photobacterium damselae).
Figure 5:
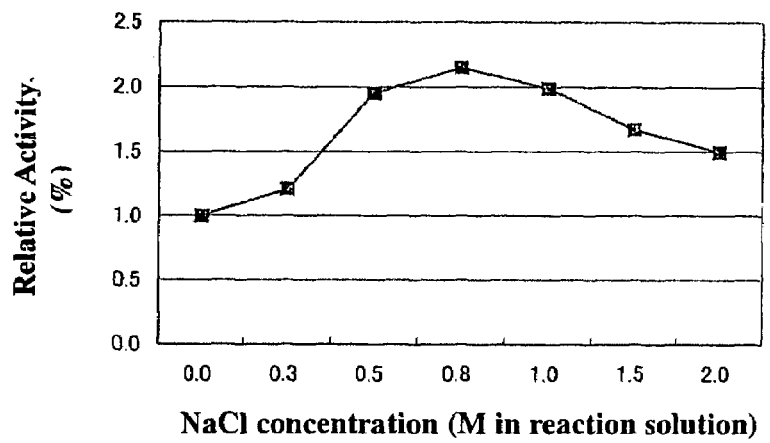
FIG. 5 is a graph showing the effect of NaCl on the enzyme activity of glycosyltransferase (α2,3-sialyltransferase; 467 native) derived from a bacterium belonging to the genus Photobacterium (Phobacterium phosphoreum).
Figure 6:
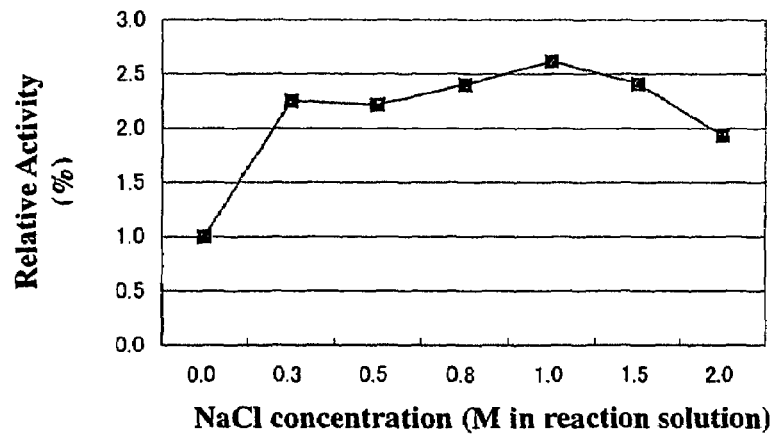
FIG. 6 is a graph showing the effect of NaCl on the enzyme activity of glycosyltransferase (recombinant α2,3-sialyltransferase; 467 N0C0) derived from a bacterium belonging to the genus Photobacterium (Phobacterium phosphoreum).
Figure 7:
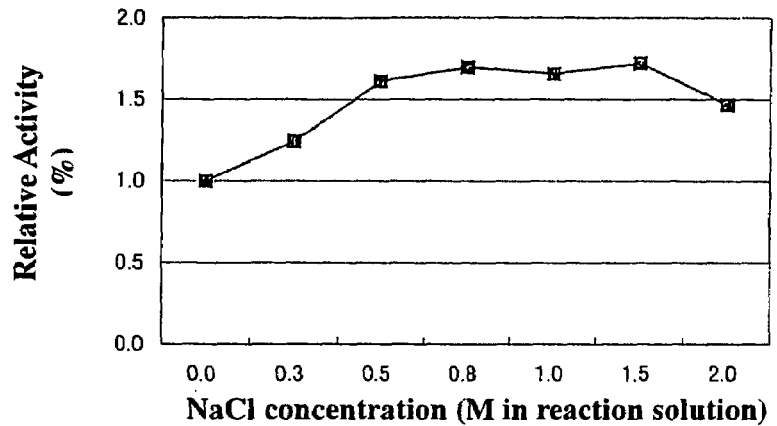
FIG. 7 is a graph showing the effect of NaCl on the enzyme activity of glycosyltransferase (recombinant α2,3-sialyltransferase; 467 N2C0) derived from a bacterium belonging to the genus Photobacterium (Phobacterium phosphoreum).
Figure 8:
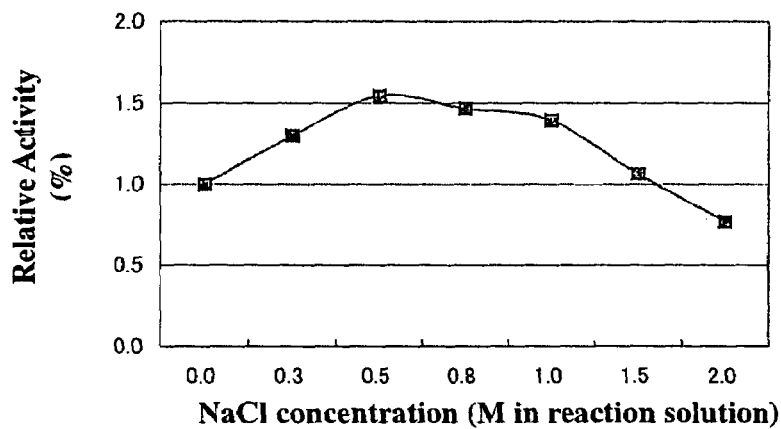
FIG. 8 is a graph showing the effect of NaCl on the enzyme activity of glycosyltransferase (recombinant α2,3-sialyltransferase; 224 N1C0) derived from a bacterium belonging to the genus Photobacterium (Phobacterium sp.).
Figure 9:
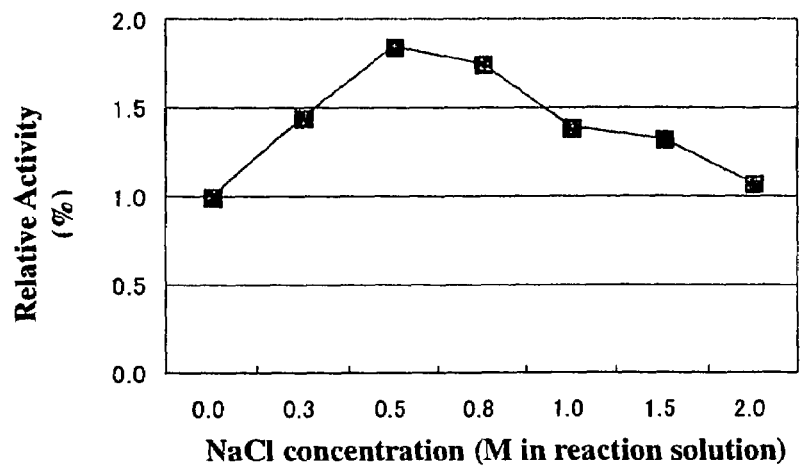
FIG. 9 is a graph showing the effect of NaCl on the enzyme activity of glycosyltransferase (recombinant α2,3-sialyltransferase; FAJ N1C0) derived from a bacterium belonging to the genus Vibrio (Vibrio sp.).

As a result, in the presence of 0.2 to 1.5 M NaCl in the reaction solution, the enzyme activity was found to be activated when compared to the absence of NaCl (FIG. 4).

Example 7

Effect of NaCl on Enzyme Activity of glycosyltransferase (Recombinant α2,3-sialyltransferase) Derived From Microorganisms of the Vibrionaceae Material and Method The effect of NaCl on enzyme activity was examined for the following enzymes: α2,3-sialyltransferase extracted and purified from *Photobacterium phosphoreum* strain JT-ISH-467 (467 native); recombinant α2,3-sialyltransferase derived from the JT-ISH-467 strain (467 N0C0 or 467 N2C0); recombinant α2,3-sialyltransferase derived from *Photobacterium* sp. strain JT-ISH-224 (224 N1C0); and recombinant α2,3-sialyltransferase derived from *Vibrio* sp. strain JT-FAJ-16 (FAJ N1C0). All recombinants used were purified before use, enough to show a single band in SDS-polyacrylamide gel electrophoresis.

For 467 N2C0, 224 N1C0 and FAJ N1C0, the enzyme reaction was accomplished in 30 µl reaction solution containing 1 µl of 1 M cacodylate buffer (pH 5.5), CMP-$^{14}$C-NeuAc as a glycosyl donor substrate (70.041 nmol, 25400 cpm), lactose as a glycosyl acceptor substrate (2.88 µmol), sialyltransferase (about 2 mU) and NaCl at a concentration varying from 0 to 2.0 M (25° C., 5 minutes). For 467 native and 467 N0C0, the enzyme reaction was accomplished in 30 µl reaction solution containing CMP-$^{14}$C-NeuAc as a glycosyl donor substrate (7.041 nmol, 25400 cpm), lactose as a glycosyl acceptor substrate (2.88 µmol), sialyltransferase (about 250 µU) and NaCl at a concentration varying from 0 to 2.0 M (25° C., 5 minutes). After completion of the enzyme reaction, the radioactivity of NeuAc which was transferred to lactose under the respective conditions was measured to calculate the enzyme activity, thereby studying the effect of NaCl on the enzyme activity in each test range.

More specifically, after completion of the reaction, each reaction solution was supplemented with 1.98 ml of 5 mM phosphate buffer (pH 6.8) and applied to a AG1−x2Resin ($PO_4^{3-}$ form, 0.2×2 cm) column. The eluate (0 to 2 ml) from this column was measured for its radioactivity. The eluate from this column contains unreacted lactose and $^{14}$C-NeuAc (N-acetylneuraminic acid)-bound sialyllactose which was generated by the reaction, but unreacted CMP-$^{14}$C-NeuAc is still retained on the column. Thus, the radioactivity of $^{14}$C from sialyllactose generated as a result of the enzymatic reaction arises exclusively from the reaction product, so that the radioactivity of this fraction can be used to calculate the enzyme activity.

Results

The results obtained for 467 native, 467 N0C0, 467 N2C0, 224 N1C0 and FAJ N1C0 are shown in FIGS. 5 to 9, respectively. The native sialyltransferase or recombinant sialyltransferases derived from *Photobacterium phosphoreum* strain JT-ISH-467, *Photobacterium* sp. strain JT-ISH-224 and *Vibrio* sp. strain JT-FAJ-16 were all found to enhance their enzyme activity due to the presence of NaCl in their enzymatic reaction systems. In the presence of NaCl at a concentration of 0.2 M to 1.5 M in their enzymatic reaction systems, their enzyme activity was improved by about 1.5- to 2.6-fold when compared to the absence of NaCl.

```
                         SEQUENCE LISTIG

<160> NUMBER OF SEQ ID NOS: 45

<210> SEQ ID NO 1
<211> LENGTH: 1230
<212> TYPE: DNA
<213> ORGANISM: Photobacterium phosphoreum
<220> FEATURE:
<221> NAME/KEY: CDS
<222> LOCATION: (1)..(1230)
<223> OTHER INFORMATION: /gene="467-23ST"
      /product="beta-galactoside-alpha2,3-sialyltransferase"

<400> SEQUENCE: 1 atg ttc gtt ttt tgt aaa aaa ata ttt ttt ttg att ttt att tca cta      48
Met Phe Val Phe Cys Lys Lys Ile Phe Phe Leu Ile Phe Ile Ser Leu
1               5                   10                  15 atg att ctg ggg ggc tgt aat agt gac tct aag cac aat aac tca gat      96
Met Ile Leu Gly Gly Cys Asn Ser Asp Ser Lys His Asn Asn Ser Asp
            20                  25                  30 ggt aat att aca aaa aat aaa aca ata gaa gtt tat gtt gat aga gca     144
Gly Asn Ile Thr Lys Asn Lys Thr Ile Glu Val Tyr Val Asp Arg Ala
        35                  40                  45 aca tta cca act att caa caa atg act cag att att aat gaa aat tca     192
Thr Leu Pro Thr Ile Gln Gln Met Thr Gln Ile Ile Asn Glu Asn Ser
    50                  55                  60 aat aat aag aaa ctt att tct tgg tct cga tac cct att aat gat gaa     240
Asn Asn Lys Lys Leu Ile Ser Trp Ser Arg Tyr Pro Ile Asn Asp Glu
65                  70                  75                  80 acg tta tta gaa tca att aat gga tca ttt ttt aaa aat agg cca gag     288
Thr Leu Leu Glu Ser Ile Asn Gly Ser Phe Phe Lys Asn Arg Pro Glu
                85                  90                  95 cta att aaa tct ctt gat tct atg ata ctt act aat gag att aaa aaa     336
Leu Ile Lys Ser Leu Asp Ser Met Ile Leu Thr Asn Glu Ile Lys Lys
            100                 105                 110 gta atc att aat ggt aat acc tta tgg gca gta gat gtc gtt aat att     384
Val Ile Ile Asn Gly Asn Thr Leu Trp Ala Val Asp Val Val Asn Ile
        115                 120                 125 ata aaa tca att gaa gct ctt gga aaa aaa aca gag att gaa cta aat     432
Ile Lys Ser Ile Glu Ala Leu Gly Lys Lys Thr Glu Ile Glu Leu Asn
    130                 135                 140 ttt tat gat gac ggt agt gca gaa tat gtt cga tta tat gac ttt tca     480
Phe Tyr Asp Asp Gly Ser Ala Glu Tyr Val Arg Leu Tyr Asp Phe Ser
145                 150                 155                 160 aga tta cct gaa tca gaa caa gaa tat aaa ata tcc tta tca aag gat     528
Arg Leu Pro Glu Ser Glu Gln Glu Tyr Lys Ile Ser Leu Ser Lys Asp
                165                 170                 175 aac att caa tca agt ata aat gga act caa cca ttt gat aac tca att     576
Asn Ile Gln Ser Ser Ile Asn Gly Thr Gln Pro Phe Asp Asn Ser Ile
            180                 185                 190 gaa aat atc tat ggc ttt tcg cag tta tac cca aca aca tat cat atg     624
Glu Asn Ile Tyr Gly Phe Ser Gln Leu Tyr Pro Thr Thr Tyr His Met
        195                 200                 205 ctc aga gca gat att ttt gaa act aat tta cct ttg acc tct ttg aaa     672
Leu Arg Ala Asp Ile Phe Glu Thr Asn Leu Pro Leu Thr Ser Leu Lys
    210                 215                 220 aga gta ata tca aat aat att aag caa atg aaa tgg gat tat ttt aca     720
Arg Val Ile Ser Asn Asn Ile Lys Gln Met Lys Trp Asp Tyr Phe Thr
```

```
act ttt aat tcc caa cag aag aat aaa ttc tat aat ttc acg gga ttt      768
Thr Phe Asn Ser Gln Gln Lys Asn Lys Phe Tyr Asn Phe Thr Gly Phe
                245                 250                 255 aac cca gaa aaa att aag gaa caa tat aaa gca agc cct cat gaa aat      816
Asn Pro Glu Lys Ile Lys Glu Gln Tyr Lys Ala Ser Pro His Glu Asn
            260                 265                 270 ttt att ttt atc gga act aat tca gga aca gca acg gca gag caa caa      864
Phe Ile Phe Ile Gly Thr Asn Ser Gly Thr Ala Thr Ala Glu Gln Gln
        275                 280                 285 ata gat att ctt aca gaa gct aaa aag cca gat agc ccg ata ata act      912
Ile Asp Ile Leu Thr Glu Ala Lys Lys Pro Asp Ser Pro Ile Ile Thr
    290                 295                 300 aat tca att caa gga ttg gat ttg ttt ttc aaa gga cat ccg agt gca      960
Asn Ser Ile Gln Gly Leu Asp Leu Phe Phe Lys Gly His Pro Ser Ala
305                 310                 315                 320 act tat aat caa caa atc att gat gct cat aat atg att gaa att tat     1008
Thr Tyr Asn Gln Gln Ile Ile Asp Ala His Asn Met Ile Glu Ile Tyr
                325                 330                 335 aat aag ata cca ttt gaa gct cta ata atg act gat gca ttg cct gat     1056
Asn Lys Ile Pro Phe Glu Ala Leu Ile Met Thr Asp Ala Leu Pro Asp
            340                 345                 350 gct gtc ggt gga atg gga agt tcg gta ttt ttt agc ttg cca aat aca     1104
Ala Val Gly Gly Met Gly Ser Ser Val Phe Phe Ser Leu Pro Asn Thr
        355                 360                 365 gta gag aat aaa ttt att ttt tat aaa agt gat acg gat att gaa aat     1152
Val Glu Asn Lys Phe Ile Phe Tyr Lys Ser Asp Thr Asp Ile Glu Asn
    370                 375                 380 aat gct ctt ata caa gta atg att gaa ctg aat atc gtt aat aga aat     1200
Asn Ala Leu Ile Gln Val Met Ile Glu Leu Asn Ile Val Asn Arg Asn
385                 390                 395                 400 gat gtt aag ttg ata agt gat ttg cag taa                             1230
Asp Val Lys Leu Ile Ser Asp Leu Gln
                405
```

<210> SEQ ID NO 2
<211> LENGTH: 409
<212> TYPE: PRT
<213> ORGANISM: Photobacterium phosphoreum

<400> SEQUENCE: 2

```
Met Phe Val Phe Cys Lys Lys Ile Phe Phe Leu Ile Phe Ile Ser Leu
1               5                   10                  15

Met Ile Leu Gly Gly Cys Asn Ser Asp Ser Lys His Asn Asn Ser Asp
                20                  25                  30

Gly Asn Ile Thr Lys Asn Lys Thr Ile Glu Val Tyr Val Asp Arg Ala
            35                  40                  45

Thr Leu Pro Thr Ile Gln Gln Met Thr Gln Ile Ile Asn Glu Asn Ser
        50                  55                  60

Asn Asn Lys Lys Leu Ile Ser Trp Ser Arg Tyr Pro Ile Asn Asp Glu
65                  70                  75                  80

Thr Leu Leu Glu Ser Ile Asn Gly Ser Phe Phe Lys Asn Arg Pro Glu
                85                  90                  95

Leu Ile Lys Ser Leu Asp Ser Met Ile Leu Thr Asn Glu Ile Lys Lys
            100                 105                 110

Val Ile Ile Asn Gly Asn Thr Leu Trp Ala Val Asp Val Val Asn Ile
        115                 120                 125

Ile Lys Ser Ile Glu Ala Leu Gly Lys Lys Thr Glu Ile Glu Leu Asn
```

-continued

```
                130                 135                 140
Phe Tyr Asp Asp Gly Ser Ala Glu Tyr Val Arg Leu Tyr Asp Phe Ser
145                 150                 155                 160

Arg Leu Pro Glu Ser Glu Gln Glu Tyr Lys Ile Ser Leu Ser Lys Asp
                165                 170                 175

Asn Ile Gln Ser Ser Ile Asn Gly Thr Gln Pro Phe Asp Asn Ser Ile
                180                 185                 190

Glu Asn Ile Tyr Gly Phe Ser Gln Leu Tyr Pro Thr Thr Tyr His Met
                195                 200                 205

Leu Arg Ala Asp Ile Phe Glu Thr Asn Leu Pro Leu Thr Ser Leu Lys
210                 215                 220

Arg Val Ile Ser Asn Asn Ile Lys Gln Met Lys Trp Asp Tyr Phe Thr
225                 230                 235                 240

Thr Phe Asn Ser Gln Gln Lys Asn Lys Phe Tyr Asn Phe Thr Gly Phe
                245                 250                 255

Asn Pro Glu Lys Ile Lys Glu Gln Tyr Lys Ala Ser Pro His Glu Asn
                260                 265                 270

Phe Ile Phe Ile Gly Thr Asn Ser Gly Thr Ala Thr Ala Glu Gln Gln
                275                 280                 285

Ile Asp Ile Leu Thr Glu Ala Lys Lys Pro Asp Ser Pro Ile Ile Thr
                290                 295                 300

Asn Ser Ile Gln Gly Leu Asp Leu Phe Phe Lys Gly His Pro Ser Ala
305                 310                 315                 320

Thr Tyr Asn Gln Gln Ile Ile Asp Ala His Asn Met Ile Glu Ile Tyr
                325                 330                 335

Asn Lys Ile Pro Phe Glu Ala Leu Ile Met Thr Asp Ala Leu Pro Asp
                340                 345                 350

Ala Val Gly Gly Met Gly Ser Ser Val Phe Phe Ser Leu Pro Asn Thr
                355                 360                 365

Val Glu Asn Lys Phe Ile Phe Tyr Lys Ser Asp Thr Asp Ile Glu Asn
                370                 375                 380

Asn Ala Leu Ile Gln Val Met Ile Glu Leu Asn Ile Val Asn Arg Asn
385                 390                 395                 400

Asp Val Lys Leu Ile Ser Asp Leu Gln
                405
```

<210> SEQ ID NO 3
<211> LENGTH: 1397
<212> TYPE: DNA
<213> ORGANISM: Photobacterium phosphoreum

<400> SEQUENCE: 3

```
gctgacgagc ggcggacggg tgagtaatgc ctgggaatat accctgatgt gggggataac    60
tattggaaac gatagctaat accgcataat ctcttcggag caaagagggg gaccttcggg   120
cctctcgcgt caggattagc ccaggtggga ttagctagtt ggtgggtaa tggctcacca    180
aggcgacgat ccctagctgg tctgagagga tgatcagcca cactggaact gagacacggt   240
ccagactcct acgggaggca gcagtgggga atattgcaca atgggggaaa ccctgatgca   300
gccatgccgc gtgtatgaag aaggccttcg ggttgtaaag tactttcagt tgtgaggaag   360
gcgttggagt taatagcttc agcgcttgac gttagcaaca gaagaagcac cggctaactc   420
cgtgccagca gccgcggtaa tacgagggt gcgagcgtta atcggaatta ctgggcgtaa   480
agcgcatgca ggcggtctgt taagcaagat gtgaaagccc ggggctcaac ctcggaacag   540
```

```
cattttgaac tggcagacta gagtcttgta gaggggggta gaatttcagg tgtagcggtg    600
aaatgcgtag agatctgaag gaataccggt ggcgaaggcg gcccctgga caaagactga    660 cgctcagatg cgaaagcgtg gggagcaaac aggattagat accctggtag tccacgccgt    720
aaacgatgtc tacttgaagg ttgtggcctt gagccgtggc tttcggagct aacgcgttaa    780
gtagaccgcc tggggagtac ggtcgcaaga ttaaaactca aatgaattga cgggggcccg    840
cacaagcggt ggagcatgtg gtttaattcg atgcaacgcg aagaacctta cctactcttg    900
acatccagag aattcgctag agatagctta gtgccttcgg gaactctgag acaggtgctg    960
catggctgtc gtcagctcgt gttgtgaaat gttgggttaa gtcccgcaac gagcgcaacc   1020
cttatccttg tttgccagca cgtaatggtg gaactccag ggagactgcc ggtgataaac   1080
cggaggaagg tggggacgac gtcaagtcat catggccctt acgagtaggg ctacacacgt   1140
gctacaatgg cgtatacaga gggctgcaag ctagcgatag tgagcgaatc ccacaaagta   1200
cgtcgtagtc cggattggag tctgcaactc gactccatga agtcggaatc gctagtaatc   1260
gtgaatcaga atgtcacggt gaatacgttc ccgggccttg tacacaccgc ccgtcacacc   1320
atgggagtgg gctgcaccag aagtagatag cttaaccttc gggagggcgt ttaccacggt   1380
gtggttcatg actgggg                                                   1397
```

<210> SEQ ID NO 4
<211> LENGTH: 10
<212> TYPE: PRT
<213> ORGANISM: Photobacterium phosphoreum
<220> FEATURE:
<221> NAME/KEY: MISC_FEATURE
<222> LOCATION: (1)..(1)
<223> OTHER INFORMATION: Xaa refers to any amino acid

<400> SEQUENCE: 4

Xaa Asn Ser Asp Ser Lys His Asn Asn Ser
1               5                   10

<210> SEQ ID NO 5
<211> LENGTH: 12
<212> TYPE: PRT
<213> ORGANISM: Photobacterium phosphoreum

<400> SEQUENCE: 5

Ser Leu Asp Ser Met Ile Leu Thr Asn Glu Ile Lys
1               5                   10

<210> SEQ ID NO 6
<211> LENGTH: 10
<212> TYPE: PRT
<213> ORGANISM: Photobacterium phosphoreum

<400> SEQUENCE: 6

Phe Tyr Asn Phe Thr Gly Phe Asn Pro Glu
1               5                   10

<210> SEQ ID NO 7
<211> LENGTH: 21
<212> TYPE: PRT
<213> ORGANISM: Photobacterium phosphoreum

<400> SEQUENCE: 7

Gly His Pro Ser Ala Thr Tyr Asn Gln Gln Ile Ile Asp Ala His Asn
1               5                   10                  15

Met Ile Glu Ile Tyr

```
<210> SEQ ID NO 8
<211> LENGTH: 23
<212> TYPE: DNA
<213> ORGANISM: Artificial Sequence
<220> FEATURE:
<223> OTHER INFORMATION: Synthetic primer 467N-RV
<220> FEATURE:
<221> NAME/KEY: misc_feature
<222> LOCATION: (6)..(6)
<223> OTHER INFORMATION: n at position 6 is inosine
<220> FEATURE:
<221> NAME/KEY: misc_feature
<222> LOCATION: (12)..(12)
<223> OTHER INFORMATION: n at position 12 is inosine

<400> SEQUENCE: 8
aaywsngayw snaarcayaa yaa                                           23

<210> SEQ ID NO 9
<211> LENGTH: 20
<212> TYPE: DNA
<213> ORGANISM: Artificial Sequence
<220> FEATURE:
<223> OTHER INFORMATION: Synthetic primer 467N-RV2
<220> FEATURE:
<221> NAME/KEY: misc_feature
<222> LOCATION: (6)..(6)
<223> OTHER INFORMATION: n at position 6 refers to inosine

<400> SEQUENCE: 9
gaywsnaarc ayaayaayws                                               20

<210> SEQ ID NO 10
<211> LENGTH: 23
<212> TYPE: DNA
<213> ORGANISM: Artificial Sequence
<220> FEATURE:
<223> OTHER INFORMATION: Synthetic primer 467N-RV3
<220> FEATURE:
<221> NAME/KEY: misc_feature
<222> LOCATION: (6)..(6)
<223> OTHER INFORMATION: n at position 6 refers to a, g, c, or t
<220> FEATURE:
<221> NAME/KEY: misc_feature
<222> LOCATION: (12)..(12)
<223> OTHER INFORMATION: n at position 6 refers to inosine

<400> SEQUENCE: 10
aaywsngayw snaarcayaa yaa                                           23

<210> SEQ ID NO 11
<211> LENGTH: 21
<212> TYPE: DNA
<213> ORGANISM: Artificial Sequence
<220> FEATURE:
<223> OTHER INFORMATION: Synthetic primer 467in1RV
<220> FEATURE:
<221> NAME/KEY: misc_feature
<222> LOCATION: (12)..(12)
<223> OTHER INFORMATION: n at position 12 refers to a, g, c, or t

<400> SEQUENCE: 11
athathgayg cncayaayat g                                             21

<210> SEQ ID NO 12
<211> LENGTH: 21
<212> TYPE: DNA
<213> ORGANISM: Artificial Sequence
```

```
<220> FEATURE:
<223> OTHER INFORMATION: Synthetic primer 467in1FW
<220> FEATURE:
<221> NAME/KEY: misc_feature
<222> LOCATION: (10)..(10)
<223> OTHER INFORMATION: n at position 10 refers to a, g, c, or t

<400> SEQUENCE: 12
catrttrtgn gcrtcdatda t                                                 21

<210> SEQ ID NO 13
<211> LENGTH: 23
<212> TYPE: DNA
<213> ORGANISM: Artificial Sequence
<220> FEATURE:
<223> OTHER INFORMATION: Synthetic primer 467in1RV2

<400> SEQUENCE: 13
tayaaycarc arathathga ygc                                               23

<210> SEQ ID NO 14
<211> LENGTH: 23
<212> TYPE: DNA
<213> ORGANISM: Artificial Sequence
<220> FEATURE:
<223> OTHER INFORMATION: Synthetic primer 467in1FW2

<400> SEQUENCE: 14
gcrtcdatda tytgytgrtt rta                                               23

<210> SEQ ID NO 15
<211> LENGTH: 23
<212> TYPE: DNA
<213> ORGANISM: Artificial Sequence
<220> FEATURE:
<223> OTHER INFORMATION: Synthetic primer 467in2RV
<220> FEATURE:
<221> NAME/KEY: misc_feature
<222> LOCATION: (12)..(12)
<223> OTHER INFORMATION: n at position 12 refers to a, c, g, or t
<220> FEATURE:
<221> NAME/KEY: misc_feature
<222> LOCATION: (15)..(15)
<223> OTHER INFORMATION: n at position 15 refers to a, c, g, or t

<400> SEQUENCE: 15
tayaayttya cnggnttyaa ycc                                               23

<210> SEQ ID NO 16
<211> LENGTH: 23
<212> TYPE: DNA
<213> ORGANISM: Artificial Sequence
<220> FEATURE:
<223> OTHER INFORMATION: Synthetic primer 467in2FW
<220> FEATURE:
<221> NAME/KEY: misc_feature
<222> LOCATION: (9)..(9)
<223> OTHER INFORMATION: n at position 9 refers to a, c, g, or t
<220> FEATURE:
<221> NAME/KEY: misc_feature
<222> LOCATION: (12)..(12)
<223> OTHER INFORMATION: n at position 12 refers to a, c, g, or t

<400> SEQUENCE: 16
ggrttraanc cngtraartt rta                                               23

<210> SEQ ID NO 17
<211> LENGTH: 929
<212> TYPE: DNA
```

<213> ORGANISM: Photobacterium phosphoreum
<220> FEATURE:
<221> NAME/KEY: misc_feature
<222> LOCATION: (39)..(39)
<223> OTHER INFORMATION: n at position 39 refers to a, c, g, or t

<400> SEQUENCE: 17

```
aactggactg gaagcattat aactcagatg gtaatattnc aaaaaataaa ccaatagaag    60
tttatgttga tagagcaaca ttaccaacta ttcaacaaat gactcagatt attaatgaaa   120
attcaaataa taagaaactt atttcttggt ctcgataccc tattaatgat gaaacgttat   180
tagaatcaat taatggatca ttttttaaaa ataggccaga gctaattaaa tctcttgatt   240
ctatgatact tactaatgag attaaaaaag taatcattaa tggtaatacc ttatgggcag   300
tagatgtcgt taatattata aaatcaattg aagctcttgg aaaaaaaaca gagattgaac   360
taaattttta tgatgacggt agtgcagaat atgttcgatt atatgacttt tcaagattac   420
ctgaatcaga acaagaatat aaaatatcct tatcaaagga taacattcaa tcaagtataa   480
atggaactca accatttgat aactcaattg aaaatatcta tggcttttcg cagttatacc   540
caacaacata tcatatgctc agagcagata tttttgaaac taatttacct ttgacctctt   600
tgaaaagagt aatatcaaat aatattaagc aaatgaaatg ggattatttt acaacttttta  660
attcccaaca gaagaataaa ttctataatt tcacggatt taacccagaa aaaattaagg   720
aacaatataa agcaagccct catgaaaatt ttatttttat cggaactaat tcaggaacag   780
caacggcaga gcaacaaata gatattctta cagaagctaa aaagccagat agcccgataa   840
taactaattc aattcaagga ttggatttgt ttttcaaagg acatccgagt gcaacttata   900
atcaacaaat catcgacgcg cacaacatg                                     929
```

<210> SEQ ID NO 18
<211> LENGTH: 21
<212> TYPE: DNA
<213> ORGANISM: Artificial Sequence
<220> FEATURE:
<223> OTHER INFORMATION: Synthetic primer 467-23STinRV1

<400> SEQUENCE: 18

```
tgttgataga gcaacattac c                                              21
```

<210> SEQ ID NO 19
<211> LENGTH: 20
<212> TYPE: DNA
<213> ORGANISM: Artificial Sequence
<220> FEATURE:
<223> OTHER INFORMATION: Synthetic primer 467-23STinRV2

<400> SEQUENCE: 19

```
tggtaatacc ttatgggcag                                                20
```

<210> SEQ ID NO 20
<211> LENGTH: 18
<212> TYPE: DNA
<213> ORGANISM: Artificial Sequence
<220> FEATURE:
<223> OTHER INFORMATION: Synthetic primer 467-23STinRV3

<400> SEQUENCE: 20

```
gaacagcaac ggcagagc                                                  18
```

<210> SEQ ID NO 21
<211> LENGTH: 21

```
<212> TYPE: DNA
<213> ORGANISM: Artificial Sequence
<220> FEATURE:
<223> OTHER INFORMATION: Synthetic primer 467-23STinRV4

<400> SEQUENCE: 21
ctaattcaat tcaaggattg g                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic primer 467-23STinFW1

<400> SEQUENCE: 22
tggtaatgtt gctctatcaa c                                              21

<210> SEQ ID NO 23
<211> LENGTH: 20
<212> TYPE: DNA
<213> ORGANISM: Artificial Sequence
<220> FEATURE:
<223> OTHER INFORMATION: Synthetic primer 467-23STinFW2

<400> SEQUENCE: 23
actgcccata aggtattacc                                                20

<210> SEQ ID NO 24
<211> LENGTH: 18
<212> TYPE: DNA
<213> ORGANISM: Artificial Sequence
<220> FEATURE:
<223> OTHER INFORMATION: Synthetic primer 467-23STinFW3

<400> SEQUENCE: 24
gctctgccgt tgctgttc                                                  18

<210> SEQ ID NO 25
<211> LENGTH: 35
<212> TYPE: DNA
<213> ORGANISM: Artificial Sequence
<220> FEATURE:
<223> OTHER INFORMATION: Synthetic primer 467-23ST-N2-Nco

<400> SEQUENCE: 25
gggctgtacc atggactcta agcacaataa ctcag                               35

<210> SEQ ID NO 26
<211> LENGTH: 36
<212> TYPE: DNA
<213> ORGANISM: Artificial Sequence
<220> FEATURE:
<223> OTHER INFORMATION: Synthetic primer 467-23ST-CO-Bm

<400> SEQUENCE: 26
cttagaatgg atccttactg caaatcactt atcaac                              36

<210> SEQ ID NO 27
<211> LENGTH: 34
<212> TYPE: DNA
<213> ORGANISM: Artificial sequence
<220> FEATURE:
<223> OTHER INFORMATION: Synthetic primer 467-23ST-N0-Pci

<400> SEQUENCE: 27
```
aagggaatac atgttcgttt tttgtaaaaa aata    34

<210> SEQ ID NO 28
<211> LENGTH: 1230
<212> TYPE: DNA
<213> ORGANISM: Photobacterium sp.
<220> FEATURE:
<221> NAME/KEY: CDS
<222> LOCATION: (1)..(1230)
<223> OTHER INFORMATION: /gene="224-23ST"
       /product="beta-galactoside-alpha-2,3-sialyltransferase"

<400> SEQUENCE: 28

```
atg ctc gtt ttt tgt aaa aaa atg ttt ttt tca gtt ttt att tca cta      48
Met Leu Val Phe Cys Lys Lys Met Phe Phe Ser Val Phe Ile Ser Leu
1               5                   10                  15 atg att ctt ggg gga tgt aat agt gac tct aat cac aat aac tca gat      96
Met Ile Leu Gly Gly Cys Asn Ser Asp Ser Asn His Asn Asn Ser Asp
            20                  25                  30 gga aat att aca aaa aat aaa aca ata gaa gtt tat gtt gat aga gca     144
Gly Asn Ile Thr Lys Asn Lys Thr Ile Glu Val Tyr Val Asp Arg Ala
        35                  40                  45 aca tta cca act att caa caa atg act cag att att aat gaa aat tca     192
Thr Leu Pro Thr Ile Gln Gln Met Thr Gln Ile Ile Asn Glu Asn Ser
    50                  55                  60 aat aac aaa aaa ctg att tct tgg tca cga tac cct att aat gat gaa     240
Asn Asn Lys Lys Leu Ile Ser Trp Ser Arg Tyr Pro Ile Asn Asp Glu
65                  70                  75                  80 gag tta ttg gaa tca att aat ggc tca ttt ttt aaa aat aat tca gag     288
Glu Leu Leu Glu Ser Ile Asn Gly Ser Phe Phe Lys Asn Asn Ser Glu
                85                  90                  95 cta att aag tct ctt gat tct atg ata ctt act aat gat ata aaa aaa     336
Leu Ile Lys Ser Leu Asp Ser Met Ile Leu Thr Asn Asp Ile Lys Lys
            100                 105                 110 gta atc atc aac ggt aat acc tta tgg gca gca gat gtc gtt aat att     384
Val Ile Ile Asn Gly Asn Thr Leu Trp Ala Ala Asp Val Val Asn Ile
        115                 120                 125 ata aaa tca att gaa gct ttt gga aaa aaa aca gaa ata gaa cta aat     432
Ile Lys Ser Ile Glu Ala Phe Gly Lys Lys Thr Glu Ile Glu Leu Asn
    130                 135                 140 ttt tat gat gat ggt agt gcg gaa tat gtt cgt tta tat gac ttt tca     480
Phe Tyr Asp Asp Gly Ser Ala Glu Tyr Val Arg Leu Tyr Asp Phe Ser
145                 150                 155                 160 aaa tta cca gaa tca gaa cag gaa tat aaa att tct ttg tca aag gat     528
Lys Leu Pro Glu Ser Glu Gln Glu Tyr Lys Ile Ser Leu Ser Lys Asp
                165                 170                 175 aac att ctt tca agt ata aat gga act caa cca ttt gaa aat gtt gtt     576
Asn Ile Leu Ser Ser Ile Asn Gly Thr Gln Pro Phe Glu Asn Val Val
            180                 185                 190 gaa aac att tat ggt ttt tct cag tta tac cca acg aca tat cat atg     624
Glu Asn Ile Tyr Gly Phe Ser Gln Leu Tyr Pro Thr Thr Tyr His Met
        195                 200                 205 ctc aga gct gat att ttt gaa act aat tta cca ttg aga tcc ttg aaa     672
Leu Arg Ala Asp Ile Phe Glu Thr Asn Leu Pro Leu Arg Ser Leu Lys
    210                 215                 220 ggg gta tta tca aat aat att aag caa atg aaa tgg gac tac ttt aaa     720
Gly Val Leu Ser Asn Asn Ile Lys Gln Met Lys Trp Asp Tyr Phe Lys
225                 230                 235                 240 act ttc aat tca cag cag aag gat aaa ttt tat aat ttt aca ggc ttt     768
Thr Phe Asn Ser Gln Gln Lys Asp Lys Phe Tyr Asn Phe Thr Gly Phe
                245                 250                 255
```

```
aac cca gac gaa att atg gag caa tat aaa gca agt cct aat aaa aac       816
Asn Pro Asp Glu Ile Met Glu Gln Tyr Lys Ala Ser Pro Asn Lys Asn
        260                 265                 270 ttt att ttt gtc ggt act aat tca gga act gca aca gca gag caa caa       864
Phe Ile Phe Val Gly Thr Asn Ser Gly Thr Ala Thr Ala Glu Gln Gln
275                 280                 285 att gat att ctg aca gaa gct aaa aat cca aat agt cct ata ata act       912
Ile Asp Ile Leu Thr Glu Ala Lys Asn Pro Asn Ser Pro Ile Ile Thr
        290                 295                 300 aaa tca att caa ggg ttt gat ttg ttt ttt aaa gga cat cct agt gca       960
Lys Ser Ile Gln Gly Phe Asp Leu Phe Phe Lys Gly His Pro Ser Ala
305                 310                 315                 320 act tat aat aaa caa atc ata gat gct cat aat atg att gaa att tat      1008
Thr Tyr Asn Lys Gln Ile Ile Asp Ala His Asn Met Ile Glu Ile Tyr
                325                 330                 335 aat aag ata cca ttt gaa gct cta atc atg act gat gca ttg cct gat      1056
Asn Lys Ile Pro Phe Glu Ala Leu Ile Met Thr Asp Ala Leu Pro Asp
            340                 345                 350 gct gtc ggt gga atg gga agt tcg gta ttt ttt agc ttg cca aat aca      1104
Ala Val Gly Gly Met Gly Ser Ser Val Phe Phe Ser Leu Pro Asn Thr
355                 360                 365 gta gag aat aaa ttt att ttt tat aaa agt gat acg gat att gaa aat      1152
Val Glu Asn Lys Phe Ile Phe Tyr Lys Ser Asp Thr Asp Ile Glu Asn
        370                 375                 380 aat gct ctt ata caa gtt atg att gaa cta aat att gtc aat aga aat      1200
Asn Ala Leu Ile Gln Val Met Ile Glu Leu Asn Ile Val Asn Arg Asn
385                 390                 395                 400 gat gtt aag ttg ata agt gat ttg cag taa                              1230
Asp Val Lys Leu Ile Ser Asp Leu Gln
                405

<210> SEQ ID NO 29
<211> LENGTH: 409
<212> TYPE: PRT
<213> ORGANISM: Photobacterium sp.

<400> SEQUENCE: 29

Met Leu Val Phe Cys Lys Lys Met Phe Phe Ser Val Phe Ile Ser Leu
1               5                   10                  15

Met Ile Leu Gly Gly Cys Asn Ser Asp Ser Asn His Asn Asn Ser Asp
            20                  25                  30

Gly Asn Ile Thr Lys Asn Lys Thr Ile Glu Val Tyr Val Asp Arg Ala
        35                  40                  45

Thr Leu Pro Thr Ile Gln Gln Met Thr Gln Ile Ile Asn Glu Asn Ser
    50                  55                  60

Asn Asn Lys Lys Leu Ile Ser Trp Ser Arg Tyr Pro Ile Asn Asp Glu
65                  70                  75                  80

Glu Leu Leu Glu Ser Ile Asn Gly Ser Phe Lys Asn Asn Ser Glu
                85                  90                  95

Leu Ile Lys Ser Leu Asp Ser Met Ile Leu Thr Asn Asp Ile Lys Lys
            100                 105                 110

Val Ile Ile Asn Gly Asn Thr Leu Trp Ala Ala Asp Val Val Asn Ile
        115                 120                 125

Ile Lys Ser Ile Glu Ala Phe Gly Lys Lys Thr Glu Ile Glu Leu Asn
    130                 135                 140

Phe Tyr Asp Asp Gly Ser Ala Glu Tyr Val Arg Leu Tyr Asp Phe Ser
145                 150                 155                 160

Lys Leu Pro Glu Ser Glu Gln Glu Tyr Lys Ile Ser Leu Ser Lys Asp
```

```
                    165                 170                 175
Asn Ile Leu Ser Ser Ile Asn Gly Thr Gln Pro Phe Glu Asn Val Val
                180                 185                 190

Glu Asn Ile Tyr Gly Phe Ser Gln Leu Tyr Pro Thr Thr Tyr His Met
            195                 200                 205

Leu Arg Ala Asp Ile Phe Glu Thr Asn Leu Pro Leu Arg Ser Leu Lys
        210                 215                 220

Gly Val Leu Ser Asn Asn Ile Lys Gln Met Lys Trp Asp Tyr Phe Lys
225                 230                 235                 240

Thr Phe Asn Ser Gln Gln Lys Asp Lys Phe Tyr Asn Phe Thr Gly Phe
                245                 250                 255

Asn Pro Asp Glu Ile Met Glu Gln Tyr Lys Ala Ser Pro Asn Lys Asn
            260                 265                 270

Phe Ile Phe Val Gly Thr Asn Ser Gly Thr Ala Thr Ala Glu Gln Gln
        275                 280                 285

Ile Asp Ile Leu Thr Glu Ala Lys Asn Pro Asn Ser Pro Ile Ile Thr
    290                 295                 300

Lys Ser Ile Gln Gly Phe Asp Leu Phe Phe Lys Gly His Pro Ser Ala
305                 310                 315                 320

Thr Tyr Asn Lys Gln Ile Ile Asp Ala His Asn Met Ile Glu Ile Tyr
                325                 330                 335

Asn Lys Ile Pro Phe Glu Ala Leu Ile Met Thr Asp Ala Leu Pro Asp
            340                 345                 350

Ala Val Gly Gly Met Gly Ser Ser Val Phe Phe Ser Leu Pro Asn Thr
        355                 360                 365

Val Glu Asn Lys Phe Ile Phe Tyr Lys Ser Asp Thr Asp Ile Glu Asn
    370                 375                 380

Asn Ala Leu Ile Gln Val Met Ile Glu Leu Asn Ile Val Asn Arg Asn
385                 390                 395                 400

Asp Val Lys Leu Ile Ser Asp Leu Gln
                405
```

<210> SEQ ID NO 30
<211> LENGTH: 1209
<212> TYPE: DNA
<213> ORGANISM: Vibrio sp.
<220> FEATURE:
<221> NAME/KEY: CDS
<222> LOCATION: (1)..(1209)
<223> OTHER INFORMATION: /gene="FAJ16-23ST"
     /product="beta-galactoside-alpha2,3-sialyltransferase"

<400> SEQUENCE: 30

```
atg aaa aac att ata aca aaa aga atg cta att att ctt tct tct cta    48
Met Lys Asn Ile Ile Thr Lys Arg Met Leu Ile Ile Leu Ser Ser Leu
1               5                   10                  15 ttc act att atc gga tgc aac aat gat aac agc act acc aca aat aac    96
Phe Thr Ile Ile Gly Cys Asn Asn Asp Asn Ser Thr Thr Thr Asn Asn
            20                  25                  30 aat gcg ata gaa ata tat gtt gat aga gcc act ctt cca act att cag   144
Asn Ala Ile Glu Ile Tyr Val Asp Arg Ala Thr Leu Pro Thr Ile Gln
        35                  40                  45 caa atg aca aaa ata gtc agt caa aaa aca agt aat aaa aaa ctt att   192
Gln Met Thr Lys Ile Val Ser Gln Lys Thr Ser Asn Lys Lys Leu Ile
    50                  55                  60 tca tgg tct aga tac cca ata act gat aaa tcg tta tta aaa aaa att   240
Ser Trp Ser Arg Tyr Pro Ile Thr Asp Lys Ser Leu Leu Lys Lys Ile
65                  70                  75                  80
```

-continued

| | |
|---|---|
| aat gca gaa ttt ttt aaa gaa caa ttt gaa tta act gaa tca cta aaa<br>Asn Ala Glu Phe Phe Lys Glu Gln Phe Glu Leu Thr Glu Ser Leu Lys<br>                  85                            90                            95 | 288 |
| aac atc ata tta agt gaa aat atc gac aac ctt ata atc cat ggt aat<br>Asn Ile Ile Leu Ser Glu Asn Ile Asp Asn Leu Ile Ile His Gly Asn<br>                100                              105                            110 | 336 |
| aca ctc tgg tct ata gat gta gta gat ata ata aaa gaa gtt aat ctc<br>Thr Leu Trp Ser Ile Asp Val Val Asp Ile Ile Lys Glu Val Asn Leu<br>        115                            120                            125 | 384 |
| ctc ggg aaa aac ata cca att gaa tta cat ttt tat gac gat ggt tca<br>Leu Gly Lys Asn Ile Pro Ile Glu Leu His Phe Tyr Asp Asp Gly Ser<br>130                              135                            140 | 432 |
| gct gaa tat gtg aga ata tac gaa ttt tca aaa ctg cct gag tca gaa<br>Ala Glu Tyr Val Arg Ile Tyr Glu Phe Ser Lys Leu Pro Glu Ser Glu<br>145                            150                            155                            160 | 480 |
| caa aaa tac aaa acg tca cta tct aaa aac aac ata aaa ttc agc ata<br>Gln Lys Tyr Lys Thr Ser Leu Ser Lys Asn Asn Ile Lys Phe Ser Ile<br>                165                              170                            175 | 528 |
| gat ggg act gat tca ttt aaa aac aca ata gaa aac att tat gga ttc<br>Asp Gly Thr Asp Ser Phe Lys Asn Thr Ile Glu Asn Ile Tyr Gly Phe<br>        180                            185                            190 | 576 |
| tca caa tta tac cca aca aca tat cac atg tta aga gcg gat ata ttc<br>Ser Gln Leu Tyr Pro Thr Thr Tyr His Met Leu Arg Ala Asp Ile Phe<br>                195                              200                            205 | 624 |
| gat aca aca tta aaa ata aac cca ttg aga gag ttg ctt tca aat aat<br>Asp Thr Thr Leu Lys Ile Asn Pro Leu Arg Glu Leu Leu Ser Asn Asn<br>210                            215                            220 | 672 |
| ata aaa caa atg aaa tgg gat tac ttt aaa gac ttt aat tat aaa caa<br>Ile Lys Gln Met Lys Trp Asp Tyr Phe Lys Asp Phe Asn Tyr Lys Gln<br>225                            230                            235                            240 | 720 |
| aaa gat att ttt tac tct ttg act aac ttc aac cca aaa gaa ata cag<br>Lys Asp Ile Phe Tyr Ser Leu Thr Asn Phe Asn Pro Lys Glu Ile Gln<br>                        245                              250                            255 | 768 |
| gaa gat ttc aac aaa aac tca aat aaa aac ttc att ttt ata gga agt<br>Glu Asp Phe Asn Lys Asn Ser Asn Lys Asn Phe Ile Phe Ile Gly Ser<br>        260                            265                            270 | 816 |
| aat agt gct aca gca aca gca gaa gag caa ata aat att att tca gaa<br>Asn Ser Ala Thr Ala Thr Ala Glu Glu Gln Ile Asn Ile Ile Ser Glu<br>275                            280                            285 | 864 |
| gca aaa aaa gaa aat agt agc att ata aca aac tct ata tca gac tat<br>Ala Lys Lys Glu Asn Ser Ser Ile Ile Thr Asn Ser Ile Ser Asp Tyr<br>        290                            295                            300 | 912 |
| gat tta ttt ttc aaa ggc cac cca agc gcc aca ttc aac gaa caa ata<br>Asp Leu Phe Phe Lys Gly His Pro Ser Ala Thr Phe Asn Glu Gln Ile<br>305                            310                            315                            320 | 960 |
| att aat gca cac gat atg atc gaa att aac aac aag atc cca ttc gaa<br>Ile Asn Ala His Asp Met Ile Glu Ile Asn Asn Lys Ile Pro Phe Glu<br>                        325                              330                            335 | 1008 |
| gcg tta ata atg aca gga ata cta cct gat gct gta ggt ggg atg ggt<br>Ala Leu Ile Met Thr Gly Ile Leu Pro Asp Ala Val Gly Gly Met Gly<br>        340                            345                            350 | 1056 |
| agt tct gtt ttc ttt agc att cca aaa gaa gtg aaa aac aaa ttt gtt<br>Ser Ser Val Phe Phe Ser Ile Pro Lys Glu Val Lys Asn Lys Phe Val<br>                355                              360                            365 | 1104 |
| ttt tat aaa agc ggt acg gat ata gaa aac aat agc cta ata caa gta<br>Phe Tyr Lys Ser Gly Thr Asp Ile Glu Asn Asn Ser Leu Ile Gln Val<br>370                            375                            380 | 1152 |
| atg cta aaa ctt aac tta ata aat cgt gac aat ata aaa cta atc agc<br>Met Leu Lys Leu Asn Leu Ile Asn Arg Asp Asn Ile Lys Leu Ile Ser | 1200 |

```
                385                 390                 395                 400
gac att taa                                                                           1209
Asp Ile <210> SEQ ID NO 31
<211> LENGTH: 402
<212> TYPE: PRT
<213> ORGANISM: Vibrio sp.

<400> SEQUENCE: 31

Met Lys Asn Ile Ile Thr Lys Arg Met Leu Ile Ile Leu Ser Ser Leu
1               5                   10                  15

Phe Thr Ile Ile Gly Cys Asn Asp Asn Ser Thr Thr Asn Asn
            20                  25                  30

Asn Ala Ile Glu Ile Tyr Val Asp Arg Ala Thr Leu Pro Thr Ile Gln
        35                  40                  45

Gln Met Thr Lys Ile Val Ser Gln Lys Thr Ser Asn Lys Lys Leu Ile
    50                  55                  60

Ser Trp Ser Arg Tyr Pro Ile Thr Asp Lys Ser Leu Leu Lys Lys Ile
65              70                  75                  80

Asn Ala Glu Phe Phe Lys Glu Gln Phe Glu Leu Thr Glu Ser Leu Lys
                85                  90                  95

Asn Ile Ile Leu Ser Glu Asn Ile Asp Asn Leu Ile His Gly Asn
            100                 105                 110

Thr Leu Trp Ser Ile Asp Val Val Asp Ile Ile Lys Glu Val Asn Leu
        115                 120                 125

Leu Gly Lys Asn Ile Pro Ile Glu Leu His Phe Tyr Asp Asp Gly Ser
    130                 135                 140

Ala Glu Tyr Val Arg Ile Tyr Glu Phe Ser Lys Leu Pro Glu Ser Glu
145                 150                 155                 160

Gln Lys Tyr Lys Thr Ser Leu Ser Lys Asn Asn Ile Lys Phe Ser Ile
                165                 170                 175

Asp Gly Thr Asp Ser Phe Lys Asn Thr Ile Glu Asn Ile Tyr Gly Phe
            180                 185                 190

Ser Gln Leu Tyr Pro Thr Thr Tyr His Met Leu Arg Ala Asp Ile Phe
        195                 200                 205

Asp Thr Thr Leu Lys Ile Asn Pro Leu Arg Glu Leu Leu Ser Asn Asn
    210                 215                 220

Ile Lys Gln Met Lys Trp Asp Tyr Phe Lys Asp Phe Asn Tyr Lys Gln
225                 230                 235                 240

Lys Asp Ile Phe Tyr Ser Leu Thr Asn Phe Asn Pro Lys Glu Ile Gln
                245                 250                 255

Glu Asp Phe Asn Lys Asn Ser Asn Lys Asn Phe Ile Phe Ile Gly Ser
            260                 265                 270

Asn Ser Ala Thr Ala Thr Ala Glu Glu Gln Ile Asn Ile Ile Ser Glu
        275                 280                 285

Ala Lys Lys Glu Asn Ser Ser Ile Ile Thr Asn Ser Ile Ser Asp Tyr
    290                 295                 300

Asp Leu Phe Phe Lys Gly His Pro Ser Ala Thr Phe Asn Glu Gln Ile
305                 310                 315                 320

Ile Asn Ala His Asp Met Ile Glu Ile Asn Asn Lys Ile Pro Phe Glu
                325                 330                 335

Ala Leu Ile Met Thr Gly Ile Leu Pro Asp Ala Val Gly Gly Met Gly
            340                 345                 350
```

```
Ser Ser Val Phe Phe Ser Ile Pro Lys Glu Val Lys Asn Lys Phe Val
        355                 360                 365

Phe Tyr Lys Ser Gly Thr Asp Ile Glu Asn Asn Ser Leu Ile Gln Val
    370                 375                 380

Met Leu Lys Leu Asn Leu Ile Asn Arg Asp Asn Ile Lys Leu Ile Ser
385                 390                 395                 400

Asp Ile

<210> SEQ ID NO 32
<211> LENGTH: 1500
<212> TYPE: DNA
<213> ORGANISM: Photobacterium sp.

<400> SEQUENCE: 32
attgaacgct ggcggcaggc ctaacacatg caagtcgagc ggtaacagat tgatagcttg      60
ctatcaatgc tgacgagcgg cggacgggtg agtaatgcct gggaatatac cctgatgtgg     120
gggataacta ttggaaacga tagctaatac cgcataatct cttcggagca agagggggga    180
ccttcgggcc tctcgcgtca ggattagccc aggtgggatt agctagttgg tggggtaatg     240
gctcaccaag gcgacgatcc ctagctggtc tgagaggatg atcagccaca ctggaactga     300
gacacggtcc agactcctac gggaggcagc agtggggaat attgcacaat ggggaaacc     360 ctgatgcagc catgccgcgt gtatgaagaa ggccttcggg ttgtaaagta ctttcagttg     420
tgaggaaggc agttaagtta atagcttagy tgtttgacgt tagcaacaga agaagcaccg     480
gctaactccg tgccagcagc cgcggtaata cggagggtgc gagcgttaat cggaattact     540
gggcgtaaag cgcatgcagg cggtctgtta agcaagatgt gaaagcccgg ggctcaacct     600
cggaacagca ttttgaactg gcagactaga gtcttgtaga gggggggtaga atttcaggtg     660 tagcggtgaa atgcgtagag atctgaagga ataccggtgg cgaaggcggc ccctggaca     720 aagactgacg ctcagatgcg aaagcgtggg gagcaaacag gattagatac cctggtagtc     780
cacgccgtaa acgatgtcta cttgaaggtt gtggccttga ccgtggctt tcggagctaa     840 cgcgttaagt agaccgcctg gggagtacgg tcgcaagatt aaaactcaaa tgaattgacg     900
ggggcccgca caagcggtgg agcatgtggt ttaattcgat gcaacgcgaa gaaccttacc     960
tactcttgac atccagagaa ttcgctagag atagcttagt gccttcggga actctgagac    1020
aggtgctgca tggctgtcgt cagctcgtgt tgtgaaatgt tgggttaagt cccgcaacga    1080
gcgcaaccct tatccttgtt tgccagcacg taatggtggg aactccaggg agactgccgg    1140
tgataaaccg gaggaaggtg gggacgacgt caagtcatca tggcccttac gagtagggct    1200
acacacgtgc tacaatggcg tatacagagg gctgcaaact agcgatagta agcgaatccc    1260
acaaagtacg tcgtagtccg gattggagtc tgcaactcga ctccatgaag tcggaatcgc    1320
tagtaatcgt gaatcagaat gtcacggtga atacgttccc gggccttgta cacaccgccc    1380
gtcacaccat gggagtgggc tgcaccagaa gtagatagct taaccttcgg gagggcgttt    1440
accacggtgt ggttcatgac tggggtgaag tcgtaacaag gtagccctag ggaacctgg    1500

<210> SEQ ID NO 33
<211> LENGTH: 1498
<212> TYPE: DNA
<213> ORGANISM: Vibrio sp.

<400> SEQUENCE: 33
attgaacgct ggcggcaggc ctaacacatg caagtcgagc ggaaacgaga agtagcttgc      60
```

```
tacttcggcg tcgagcggcg gacgggtgag taatgcatag gaagttgccc agtagagggg      120
gataaccatt ggaaacgatg gctaataccg cataacctct tcggagcaaa gcggggggacc    180 ttcgggcctc gcgctactgg atacgcctat gtgggattag ctagttggtg aggtaatggc      240
tcaccaaggc gacgatccct agctggtctg agaggatgat cagccacact gggactgaga     300
cacggcccag actcctacgg gaggcagcag tggggaatat tgcacaatgg gcgaaagcct     360
gatgcagcca tgccgcgtgt atgaagaagg ccttcgggtt gtaaagtact ttcagttgtg     420
aggaagggtg tgtagttaat aactgcgcat tttgacgtta gcaacagaag aagcaccggc     480
taactccgtg ccagcagccg cggtaatacg gagggtgcga gcgttaatcg gaattactgg     540
gcgtaaagcg catgcaggtg gtttgttaag tcagatgtga aagcccgggg ctcaacctcg     600
gaaggtcatt tgaaactggc aaactagagt actgtagagg ggggtagaat ttcaggtgta    660
gcggtgaaat gcgtagagat ctgaaggaat accagtggcg aaggcggccc cctggacaga    720
tactgacact cagatgcgaa agcgtgggga gcaaacagga ttagataccc tggtagtcca    780
cgccgtaaac gatgtctact tggaggttgt ggccttgagc cgtggctttc ggagctaacg    840
cgttaagtag accgcctggg gagtacggtc gcaagattaa aactcaaatg aattgacggg    900
ggcccgcaca agcggtggag catgtggttt aattcgatgc aacgcgaaga accttaccta    960
ctcttgacat ccagagaact ttccagagat ggattggtgc cttcgggaac tctgagacag   1020
gtgctgcatg gctgtcgtca gctcgtgttg tgaaatgttg ggttaagtcc cgcaacgagc   1080
gcaaccctta tccttgtttg ccagcgagta atgtcgggaa ctccaggag actgccggtg    1140 ataaaccgga ggaaggtggg gacgacgtca agtcatcatg gcccttacga gtagggctac   1200
acacgtgcta caatggcgca tacagagggc agcaagctag cgatagtgag cgaatcccaa    1260
aaagtgcgtc gtagtccgga ttggagtctg caactcgact ccatgaagtc ggaatcgcta    1320
gtaatcgtgg atcagaatgc cacggtgaat acgttcccgg gccttgtaca caccgcccgt    1380
cacaccatgg gagtgggctg caaaagaagt aggtagttta accttcggga ggacgcttac    1440
cactttgtgg ttcatgactg gggtgaagtc gtaacaaggt agccctaggg gaacctgg     1498

<210> SEQ ID NO 34
<211> LENGTH: 20
<212> TYPE: DNA
<213> ORGANISM: Artificial Sequence
<220> FEATURE:
<223> OTHER INFORMATION: Synthetic primer 224-23ST-inRV1

<400> SEQUENCE: 34
caggaactgc aacagcagag                                                  20

<210> SEQ ID NO 35
<211> LENGTH: 34
<212> TYPE: DNA
<213> ORGANISM: Artificial Sequence
<220> FEATURE:
<223> OTHER INFORMATION: Synthetic primer 224-23ST-N0-Pci

<400> SEQUENCE: 35
aagggaatac atgttcgttt tttgtaaaaa aatg                                  34

<210> SEQ ID NO 36
<211> LENGTH: 35
<212> TYPE: DNA
<213> ORGANISM: Artificial Sequence
<220> FEATURE:
<223> OTHER INFORMATION: Synthetic primer 224-23ST-N1-Nco
```

<400> SEQUENCE: 36
gggatgtacc atggactcta atcacaataa ctcag         35

<210> SEQ ID NO 37
<211> LENGTH: 36
<212> TYPE: DNA
<213> ORGANISM: Artificial sequence
<220> FEATURE:
<223> OTHER INFORMATION: Synthetic primer 224-23ST-C0new-Bm

<400> SEQUENCE: 37
attaaaatgg atccttactg caaatcactt atcaac        36

<210> SEQ ID NO 38
<211> LENGTH: 20
<212> TYPE: DNA
<213> ORGANISM: Artificial Sequence
<220> FEATURE:
<223> OTHER INFORMATION: Synthetic primer FAJEc3.6RV1

<400> SEQUENCE: 38
ttcaaaactg cctgagtcag         20

<210> SEQ ID NO 39
<211> LENGTH: 20
<212> TYPE: DNA
<213> ORGANISM: Artificial Sequence
<220> FEATURE:
<223> OTHER INFORMATION: Synthetic primer FAJEc3.6RV2

<400> SEQUENCE: 39
atttcatggt ctagataccc         20

<210> SEQ ID NO 40
<211> LENGTH: 20
<212> TYPE: DNA
<213> ORGANISM: Artificial Sequence
<220> FEATURE:
<223> OTHER INFORMATION: Synthetic primer FAJ23STinFW3

<400> SEQUENCE: 40
ctgactcagg cagttttgaa         20

<210> SEQ ID NO 41
<211> LENGTH: 21
<212> TYPE: DNA
<213> ORGANISM: Artificial Sequence
<220> FEATURE:
<223> OTHER INFORMATION: Synthetic primer FAJ23STinFW4

<400> SEQUENCE: 41
gaaagcaact ctctcaatgg g        21

<210> SEQ ID NO 42
<211> LENGTH: 21
<212> TYPE: DNA
<213> ORGANISM: Artificial Sequence
<220> FEATURE:
<223> OTHER INFORMATION: Synthetic primer FAJ23STinRV3

<400> SEQUENCE: 42
ataaacccat tgagagagtt g        21

<210> SEQ ID NO 43

```
<211> LENGTH: 37
<212> TYPE: DNA
<213> ORGANISM: Artificial Sequence
<220> FEATURE:
<223> OTHER INFORMATION: Synthetic primer FAJ23STN0-BspHI

<400> SEQUENCE: 43
tggataactc atgaaaaaca ttataacaaa aagaatg                              37

<210> SEQ ID NO 44
<211> LENGTH: 34
<212> TYPE: DNA
<213> ORGANISM: Artificial Sequence
<220> FEATURE:
<223> OTHER INFORMATION: Synthetic primer FAJ23STN1-BspHI

<400> SEQUENCE: 44
tattatcgtc atgaacaatg ataacagcac tacc                                 34

<210> SEQ ID NO 45
<211> LENGTH: 38
<212> TYPE: DNA
<213> ORGANISM: Artificial Sequence
<220> FEATURE:
<223> OTHER INFORMATION: Synthetic primer FAJ23STC0-BamHI

<400> SEQUENCE: 45 tcttttagg atccttaaat gtcgctgatt agttttat                              38
```

The invention claimed is:

1. A method for improving the reaction efficiency of sialylation with a sialyltransferase derived from a marine microorganism belonging to the genus *Photobacterium*, wherein said method comprises the following steps:
   (a) contacting the sialyltransferase with a glycosyl donor substrate and a glycosyl acceptor substrate in the presence of 0.1 M-2.0 M NaCl; and
   (b) carrying out the reaction in the presence of NaCl; thereby improving the reaction efficiency when compared to the absence of 0.1 M-2.0 M NaCl.

2. The method according to claim 1, wherein NaCl is present at a concentration of 0.1 M to 1.5 M.

3. The method according to claim 1, wherein NaCl is present at a concentration of 0.2 M to 1.0 M.

4. The method according to claim 1 wherein the microorganism according to the genus *Photobacterium* is *Photobacterium damselae*.

5. The method according to claim 1, wherein the sialyltransferase is β-galactoside-α2,6-sialyltransferase.

6. The method according to claim 1, wherein the sialyltransferase is β-galactoside-α2,3-sialyltransferase.

7. A method for improving the reaction efficiency of sialylation with a sialyltransferase derived from a marine microorganism belonging to the Vibrionaceae, wherein said method comprises the following steps:
   (a) contacting the sialyltransferase with a glycosyl donor substrate and a glycosyl acceptor substrate in the presence of 0.1 M-2.0 M NaCl; and
   (b) carrying out the reaction in the presence of NaCl; thereby improving the reaction efficiency when compared to the absence of 0.1 M-2.0 M NaCl.

* * * * *